US012454656B2

(12) United States Patent
Latimer et al.

(10) Patent No.: US 12,454,656 B2
(45) Date of Patent: *Oct. 28, 2025

(54) ADDITIVES WITH HIGH SULFURIZATION FOR LUBRICATING OIL COMPOSITIONS

(71) Applicant: AFTON CHEMICAL CORPORATION, Richmond, VA (US)

(72) Inventors: Mitchell Latimer, Montpellier, VA (US); Piotr Grzyska, Richmond, VA (US); Jason Bell, Powhatan, VA (US)

(73) Assignee: AFTON CHEMICAL CORPORATION

( * ) Notice: Subject to any disclaimer, the term of this patent is extended or adjusted under 35 U.S.C. 154(b) by 0 days.

This patent is subject to a terminal disclaimer.

(21) Appl. No.: 18/850,353

(22) PCT Filed: Apr. 27, 2023

(86) PCT No.: PCT/US2023/020157

§ 371 (c)(1),
(2) Date: Sep. 24, 2024

(87) PCT Pub. No.: WO2023/212165

PCT Pub. Date: Nov. 2, 2023

(65) Prior Publication Data

US 2025/0236807 A1 Jul. 24, 2025

Related U.S. Application Data

(60) Provisional application No. 63/478,724, filed on Jan. 6, 2023, provisional application No. 63/432,757, filed (Continued)

(51) Int. Cl.
*C10M 135/02* (2006.01)
*C07C 319/14* (2006.01)
(Continued)

(52) U.S. Cl.
CPC ......... *C10M 135/02* (2013.01); *C07C 319/14* (2013.01); *C10M 169/04* (2013.01);
(Continued)

(58) Field of Classification Search
CPC ............ C10N 2010/04; C10N 2030/04; C10N 2030/43; C10N 2030/52; C07C 319/18;
(Continued)

(56) References Cited

U.S. PATENT DOCUMENTS 1,065,595 A 6/1913 Demary
2,140,811 A 12/1938 Poole
(Continued)

FOREIGN PATENT DOCUMENTS

AU 404582 2/1968
EP 92415 B1 8/1985
(Continued)

OTHER PUBLICATIONS

International Search Report and Written Opinion for PCT/US2023/020157, Jul. 24, 2023.
(Continued)

*Primary Examiner* — Vishal V Vasisth
(74) *Attorney, Agent, or Firm* — Honigman LLP

(57) ABSTRACT

The present disclosure provides a method for preparing a sulfurized alkyl phenate product to achieve a high sulfurization ratio of sulfurized alkyl phenate to unsulfurized alkyl phenate/phenol in the context of a neutralized and optionally overbased additive.

20 Claims, 1 Drawing Sheet

Related U.S. Application Data on Dec. 15, 2022, provisional application No. 63/432,752, filed on Dec. 15, 2022, provisional application No. 63/335,474, filed on Apr. 27, 2022.

(51) Int. Cl.

| | |
|---|---|
| ***C10M 169/04*** | (2006.01) |
| *C10N 30/00* | (2006.01) |
| *C10N 30/02* | (2006.01) |
| *C10N 30/04* | (2006.01) |
| *C10N 40/25* | (2006.01) |

(52) U.S. Cl.
CPC ..... *C10M 2219/02* (2013.01); *C10N 2030/02* (2013.01); *C10N 2030/04* (2013.01); *C10N 2030/52* (2020.05); *C10N 2040/252* (2020.05); *C10N 2040/255* (2020.05)

(58) Field of Classification Search
CPC ............ C07C 2601/16; C10M 135/02; C10M 159/22; C10M 169/04; C10M 2203/003; C10M 2219/02; C10M 2219/089
See application file for complete search history.

(56) References Cited

U.S. PATENT DOCUMENTS 2,680,096 A 6/1954 Walker et al.
2,777,874 A 1/1957 Asseff et al.
3,178,663 A 4/1965 Kahn
3,185,647 A 5/1965 Anderson et al.
3,189,544 A 6/1965 Ratner et al.
3,256,185 A 6/1966 Le Suer
3,278,550 A 10/1966 Norman et al.
3,312,619 A 4/1967 Vineyard
3,366,569 A 1/1968 Norman et al.
3,367,867 A 2/1968 Abbott et al.
3,367,981 A 2/1968 Napolitano
3,372,116 A 3/1968 Meinhardt
3,390,086 A 6/1968 O'Halloran
3,403,102 A 9/1968 Le Suer
3,410,798 A 11/1968 Cohen
3,423,474 A 1/1969 Anderson et al.
3,458,530 A 7/1969 Siegel et al.
3,470,098 A 9/1969 O'Halloran
RE26,811 E 3/1970 Cohen
3,502,677 A 3/1970 Le Sner
3,519,564 A 7/1970 Vogel
3,546,243 A 12/1970 Keith
3,573,205 A 3/1971 Lowe et al.
3,634,515 A 1/1972 Piasek et al.
3,649,229 A 3/1972 Otto
3,704,315 A 11/1972 Strang
3,708,522 A 1/1973 Le Suer
3,749,695 A 7/1973 de Vries
3,801,507 A 4/1974 Hendrickson et al.
3,859,318 A 1/1975 Lesuer
3,865,740 A 2/1975 Goldschmidt
3,865,813 A 2/1975 Gergel
3,954,639 A 5/1976 Liston
4,021,419 A 5/1977 Karn
4,152,499 A 5/1979 Boerzel et al.
4,234,435 A 11/1980 Meinhardt et al.
4,259,194 A 3/1981 deVries et al.
4,259,195 A 3/1981 King et al.
4,261,843 A 4/1981 King et al.
4,263,152 A 4/1981 King et al.
4,265,773 A 5/1981 deVries et al.
4,272,387 A 6/1981 King et al.
4,283,295 A 8/1981 deVries et al.
4,285,822 A 8/1981 deVries et al.
4,328,111 A 5/1982 Watson et al.
4,379,064 A 4/1983 Cengel et al.
4,435,301 A 3/1984 Brannen et al.
4,482,464 A 11/1984 Karol et al.
4,521,318 A 6/1985 Karol
4,554,086 A 11/1985 Karol et al.
4,579,675 A 4/1986 Sawicki et al.
4,612,132 A 9/1986 Wollenberg et al.
4,614,522 A 9/1986 Buckley
4,614,603 A 9/1986 Wollenberg
4,617,137 A 10/1986 Plavac
4,617,138 A 10/1986 Wollenberg
4,636,322 A 1/1987 Nalesnik
4,645,515 A 2/1987 Wollenberg
4,646,860 A 3/1987 Owens et al.
4,647,390 A 3/1987 Buckley, III et al.
4,648,886 A 3/1987 Buckley, III et al.
4,648,980 A 3/1987 Erdman
4,652,387 A 3/1987 Andress, Jr. et al.
4,663,062 A 5/1987 Wollenberg
4,663,064 A 5/1987 Nalesnik et al.
4,666,459 A 5/1987 Wollenberg
4,666,460 A 5/1987 Wollenberg
4,668,246 A 5/1987 Wollenberg
4,670,170 A 6/1987 Wollenberg
4,699,724 A 10/1987 Nalesnik et al.
4,710,308 A 12/1987 Stauffer
4,713,189 A 12/1987 Nalesnik et al.
4,713,191 A 12/1987 Nalesnik
4,857,214 A 8/1989 Papay et al.
4,948,386 A 8/1990 Sung et al.
4,952,739 A 8/1990 Chen
4,963,275 A 10/1990 Gutierrez et al.
4,963,278 A 10/1990 Blain et al.
4,971,598 A 11/1990 Andress et al.
4,971,711 A 11/1990 Lundberg et al.
4,973,411 A 11/1990 Jao et al.
4,973,412 A 11/1990 Migdal et al.
4,981,492 A 1/1991 Blain et al.
5,024,773 A 6/1991 Liston
5,026,495 A 6/1991 Emert et al.
5,030,249 A 7/1991 Herbstman et al.
5,039,307 A 8/1991 Herbstman et al.
5,075,383 A 12/1991 Migdal et al.
5,124,056 A 6/1992 Gutterrez et al.
5,266,223 A 11/1993 Song et al.
5,334,321 A 8/1994 Harrison et al.
5,650,381 A 7/1997 Gatto et al.
5,739,355 A 4/1998 Gateau et al.
5,827,806 A 10/1998 Skinner
5,840,672 A 11/1998 Gatto
6,107,257 A 8/2000 Valcho et al.
6,281,320 B1 8/2001 Kao et al.
RE37,363 E 9/2001 Gatto et al.
6,300,291 B1 10/2001 Hartley et al.
6,723,685 B2 4/2004 Hartley et al.
RE38,929 E 1/2006 Gatto et al.
7,214,649 B2 5/2007 Loper et al.
7,253,231 B2 8/2007 Devlin et al.
RE40,595 E 12/2008 Gatto et al.
7,485,603 B2 2/2009 Bera et al.
7,645,726 B2 1/2010 Loper
7,732,390 B2 6/2010 Kadkhodayan et al.
7,786,057 B2 8/2010 Bera et al.
7,897,696 B2 3/2011 Huang et al.
8,048,831 B2 11/2011 Loper
8,425,629 B2 4/2013 Jackson et al.
8,513,172 B2 8/2013 Baum et al.
8,933,002 B2 1/2015 Sinquin et al.
9,453,089 B2 9/2016 Shaikh et al.
9,982,212 B2 5/2018 Fan et al.
9,988,590 B1 6/2018 Kwak
10,144,900 B1 12/2018 Kwak
11,572,523 B1 2/2023 Kondracki
2008/0182468 A1 7/2008 Dharmarajan et al.
2009/0143264 A1 6/2009 Harrison
2009/0258803 A1 10/2009 Harrison
2009/0298964 A1 12/2009 Jacob et al.
2010/0139944 A1 6/2010 Guo et al.
2010/0261808 A1 10/2010 Schadler et al.
2012/0101017 A1 4/2012 Duggal
2012/0196778 A1 8/2012 Gieselman et al.
2013/0123157 A1 5/2013 Sinquin et al.

(56) References Cited

U.S. PATENT DOCUMENTS

| | | | |
|---|---|---|---|
| 2014/0061533 | A1 | 3/2014 | Schultz Hume et al. |
| 2014/0142347 | A1 | 5/2014 | Mahieux et al. |
| 2014/0275501 | A1 | 9/2014 | Capanema et al. |
| 2015/0045269 | A1 | 2/2015 | Walker |
| 2015/0119304 | A1 | 4/2015 | Jukes |
| 2015/0344808 | A1 | 12/2015 | Lagona et al. |
| 2017/0096502 | A1 | 4/2017 | Storey et al. |
| 2017/0211008 | A1 | 7/2017 | Walker et al. |
| 2017/0335148 | A1 | 11/2017 | Chou |
| 2020/0318025 | A1 | 10/2020 | Sampler et al. |
| 2020/0377815 | A1 | 12/2020 | Sampler et al. |
| 2020/0377817 | A1 | 12/2020 | Sampler et al. |
| 2023/0235241 | A1 | 7/2023 | Kondracki |

FOREIGN PATENT DOCUMENTS

| | | | |
|---|---|---|---|
| EP | 0367386 | A3 | 7/1991 |
| EP | 0299996 | B1 | 7/1993 |
| EP | 0976813 | B1 | 12/2003 |
| EP | 1419226 | B1 | 6/2005 |
| EP | 1903093 | A1 | 3/2008 |
| EP | 3149131 | A1 | 4/2017 |
| EP | 3472274 | A2 | 4/2019 |
| GB | 785468 | A | 10/1957 |
| GB | 2140811 | A | 12/1984 |
| WO | 8805810 | A1 | 8/1988 |
| WO | 9406897 | A1 | 3/1994 |
| WO | 9414739 | A1 | 7/1994 |
| WO | 2005026299 | A2 | 3/2005 |
| WO | 2013059173 | A1 | 4/2013 |
| WO | 2021035087 | A1 | 2/2021 |
| WO | 2021161199 | A1 | 8/2021 |

OTHER PUBLICATIONS

Neale, A.J. et al., "Rearrangements and Decompositions of Thiobisphenols," Tetrahedron, vol. 25, pp. 4583-4591 (1969).

International Preliminary Report on Patentability for PCT/US2023/020157, dated Oct. 29, 2024.

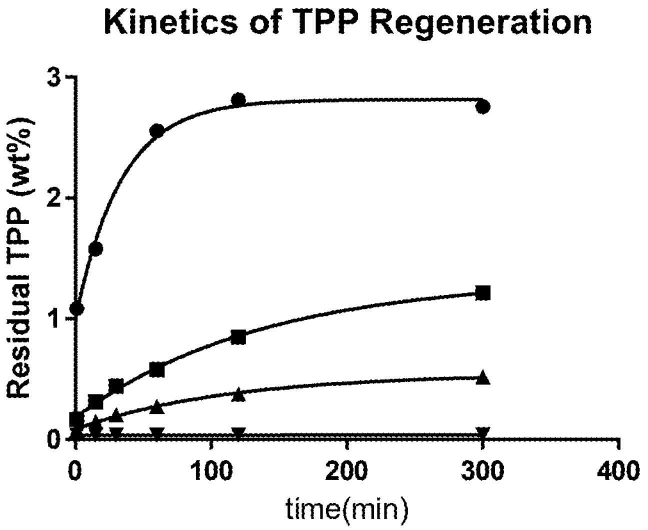
Kinetics of TPP Regeneration
Residual TPP (wt%)
0
1
2
3
0
100
200
300
400
time(min)

ADDITIVES WITH HIGH SULFURIZATION FOR LUBRICATING OIL COMPOSITIONS

RELATED APPLICATIONS

The present application is a national stage application based on PCT International Application PCT/US2023/020157 filed Apr. 27, 2023, which claims priority to U.S. Provisional Patent Application U.S. 63/335,474 filed Apr. 27, 2022, U.S. Provisional Patent Application U.S. 63/432,752 filed Dec. 15, 2022, U.S. Provisional Patent Application U.S. 63/432,757 filed Dec. 15, 2022, and U.S. Provisional Patent Application U.S. 63/478,724 filed Jan. 6, 2023; wherein the entirety of each of said Applications in incorporated herein by reference.

TECHNICAL FIELD

The present disclosure generally relates to lubricating oil compositions and additives therefor with high levels of sulfurization.

BACKGROUND

Metal salts of sulfurized alkyl phenols, otherwise known as alkyl phenates, tend to be useful lubricating oil additives. These additives may function as a detergent and/or dispersant and also provide an alkalinity base to aid in the neutralization of acids generated during automotive operation. Unsulfurized variants of the alkyl phenates have reduced utility and tend to be less desired in the lubricant for many reasons. As such, additive manufacturers seek to minimize levels of unsulfurized alkyl phenates and/or alkyl phenols in their additives. Current methods, however, have one or more shortcomings when seeking to minimize levels of unsulfurized alkyl phenate/phenol variants when the additives are also overbased.

SUMMARY AND TERMS

In accordance with one embodiment, a process for preparing a sulfurized alkyl phenate product to achieve a high sulfurization ratio of sulfurized alkyl phenate to unsulfurized alkyl phenate is described herein. In one approach, the process includes sulfurizing an alkyl phenol with a source of sulfur to provide a sulfurized alkyl phenol, wherein the alkyl phenol may be derived from an alkylation of a phenol and wherein a mol ratio of the sulfur source to the alkyl phenol is about 0.66 to about 3.5 (in other approaches, about 0.67 to about 3.5, or about 0.68 to about 3.5, or about 0.7 to about 3.5); neutralizing and optionally overbasing the sulfurized alkyl phenol in the presence of a solvent to provide a sulfurized alkyl phenate composition, wherein the neutralizing and the optional overbasing is at a temperature not exceeding about 140° C. to achieve a sulfurization ratio of about 500:1 or greater; and post processing the sulfurized alkyl phenate composition to obtain the sulfurized alkyl phenate product, wherein the post processing is at temperatures not to exceed about 140° C. to maintain the sulfurization ratio of about 500:1 or greater and, in some embodiments, wherein the sulfurized alkyl phenate product has less than about 0.2 weight percent of unsulfurized alkyl phenate and/or unsulfurized alkyl phenol, less than about 0.1 weight percent, less than about 0.08 weight percent of unsulfurized alkyl phenate and/or unsulfurized alkyl phenol, less than about 0.06 weight percent of unsulfurized alkyl phenate and/or unsulfurized alkyl phenol, less than about 0.04 weight percent of unsulfurized alkyl phenate and/or unsulfurized alkyl phenol, or less than about 0.03 weight percent of unsulfurized alkyl phenate and/or unsulfurized alkyl phenol.

In other approaches or embodiments, the process of the preceding paragraph may be combined with one or more optional features, embodiments, or process steps in any combination thereof. Such optional features and embodiments may include one or more of the following: wherein the source of sulfur includes elemental sulfur, sulfur monochloride, sulfur dichloride, hydrogen sulfide, sulfur dioxide, sulfide hydrates, or combinations thereof; and/or wherein a mol ratio of the sulfur source to the alkyl phenol is about 0.68 to about 3.5; and/or wherein a mol ratio of the sulfur source to the alkyl phenol is about 0.7 to about 2; and/or wherein the sulfur source is sulfur monochloride; and/or wherein the solvent is one more solvents having a boiling point of about 100° C. or less at about 1000 to about 40 mbars; and/or wherein the solvent is xylene, toluene, octane, butanol, heptane, methanol, acetone, benzene, cyclohexane, cyclopentane, ethanol, hexane, pentane, propanol, water, or combinations thereof; and/or wherein the neutralizing and/or the optional overbasing includes contacting the sulfurized alkyl phenol with an alkali or alkaline earth metal salt at a temperature not to exceed about 140° C.; and/or wherein the alkali or alkaline earth metal salt is lithium hydroxide, potassium hydroxide, sodium hydroxide, magnesium hydroxide, calcium hydroxide, barium hydroxide, aluminum hydroxide, lithium oxide, magnesium oxide, calcium oxide, barium oxide, or combinations thereof; and/or wherein the neutralizing and/or the optional overbasing occurs in the presence of a carbonation agent at a temperature not to exceed about 140° C.; and/or wherein the post processing includes one or more of vacuum stripping, sparging, distillation, filtering, degassing, evaporation, wiped-film evaporating, centrifuging, diluting, liquid-liquid extraction, membrane separation, chromatography, adsorption, supercritical extractions, or combinations thereof and wherein all post processing is at a temperature not to exceed about 140° C.; and/or wherein the process does not remove residual unsulfurized alkyl phenate between the sulfurizing, the neutralizing, and/or the optional overbasing; and/or wherein the temperature of the neutralizing and the optional overbasing and the temperature of the post processing does not exceed about 100° C.; and/or wherein the sulfurization ratio of the sulfurized alkyl phenate product is about 5000:1 to about 500:1; and/or wherein the sulfurization ratio of the sulfurized alkyl phenate product is about 3500:1 to about 1000:1; and/or wherein the sulfurized alkyl phenate product has a total base number of about 100 to about 400 mg KOH/g as measured by the method of ASTM D-2896; and/or wherein the sulfurized alkyl phenate product has less than about 0.2 weight percent of unsulfurized alkyl phenate or unsulfurized alkyl phenol; and/or wherein the sulfurizing occurs at a temperature of about 0 to about 250° C.; and/or wherein the sulfurizing occurs at a temperature of about 40 to about 120° C.; and/or wherein the sulfurizing occurs in the absence of a base; and/or wherein the sulfurized alkyl phenol is neutralized and overbased; and/or wherein the alkylation of the phenol is with one or more oligomers obtained from olefins; and/or wherein the olefins include ethylene, propylene, butylene, isobutylene, pentene, or combinations thereof.

In other embodiments, a sulfurized alkyl phenate product is described herein wherein the sulfurized alkyl phenate product is prepared by the methods as described by any embodiment of the previous two paragraphs.

In other embodiments, a metal phenate detergent is provided having a high sulfurization ratio of sulfurized alkyl phenate to unsulfurized alkyl phenate, In approaches, the metal phenate detergent includes a sulfurized alkyl phenate obtained from a source of sulfur and an alkyl phenol with a mol ratio of the sulfur source to the alkyl phenol of about 0.66 to about 3.5 (in other approaches, about 0.67 to about 3.5 or about 0.68 to about 3.5 or about 0.7 to about 3.5) and having a total base number of about 50 to about 400 mg KOH/g as measured by the method of ASTM D-2896; up to about 100,000 ppm of alkali or alkaline metal and up to about 65,000 ppm of sulfur; and a sulfurization ratio of about 500:1 to about 5500:1, and in some embodiments, with no more than about 900 ppm of unsulfurized alkyl phenate and/or unsulfurized alkyl phenol, no more than about 800 ppm, no more than about 700 ppm, no more than about 600 ppm, no more than about 500 ppm, no more than about 400 ppm, or no more than 300 ppm of unsulfurized alkyl phenate and/or unsulfurized alkyl phenol.

In yet other embodiments, the metal phenate detergent may include embodiments having a number of optional features in any combination. The optional features and embodiments include one or more of the following: wherein the metal is calcium and the metal phenate detergent has about 35,000 ppm to about 100,000 ppm of calcium; and/or wherein the metal phenate detergent has at least about 25,000 ppm of sulfur; and/or wherein the metal phenate detergent has at least about 30,000 ppm of sulfur; and/or wherein the sulfurization ratio is about 1200:1 to about 5000:1; and/or wherein the alkyl phenate is derived from an alkylation of a phenol with one or more C6 to C36 alkylene groups; and/or wherein the alkylene groups are oligomers; and/or wherein the oligomers are derived from ethylene, propylene, butylene, isobutylene, pentene, or combinations thereof, and/or wherein the sulfurized alkyl phenate detergent has a total base number of about 90 to about 250 mg KOH/g as measured by the method of ASTM D-2896; and/or wherein the sulfurized alkyl phenate has less than about 50 percent of alkyl substitution at the ortho position.

In yet other embodiments, a lubricating oil composition is described herein wherein the lubricating oil composition includes any embodiment of the metal phenate as described in this Summary and one or more base oils of lubricating viscosity.

In yet further embodiments, the use of low temperature processing as described in any embodiment of the methods herein is provided to form a metal phenate detergent and/or a sulfurized alkyl phenate product having a sulfurization ratio of about 500:1 or greater and, in some embodiments, less than about 0.2 weight percent of unsulfurized alkyl phenate and/or unsulfurized alkyl phenol, less than about 0.1 weight percent, less than about 0.08 weight percent of unsulfurized alkyl phenate and/or unsulfurized alkyl phenol, less than about 0.06 weight percent of unsulfurized alkyl phenate and/or unsulfurized alkyl phenol, less than about 0.04 weight percent of unsulfurized alkyl phenate and/or unsulfurized alkyl phenol, or less than about 0.03 weight percent of unsulfurized alkyl phenate and/or unsulfurized alkyl phenol The following definitions of terms are provided in order to clarify the meanings of certain terms as used herein.

The terms "oil composition," "lubrication composition," "lubricating oil composition," "lubricating oil," "lubricant composition," "lubricating composition," "fully formulated lubricant composition," and "lubricant" are considered synonymous, fully interchangeable terminology referring to the finished lubrication product comprising a major amount of a base oil plus a minor amount of an additive composition.

As used herein, the terms "additive package," "additive concentrate," and "additive composition" are considered synonymous, fully interchangeable terminology referring the portion of the lubricating oil composition excluding the major amount of base oil stock mixture.

The term "overbased" relates to metal salts, such as metal salts of sulfonates, carboxylates, salicylates, and/or phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, salicylates, sulfonates, and/or phenols.

The term "alkaline earth metal" relates to calcium, barium, magnesium, and strontium, and the term "alkali metal" refers to lithium, sodium, potassium, rubidium, and cesium.

As used herein, the term "hydrocarbyl" or "hydrocarbyl substituent" or "hydrocarbyl group" is used in its ordinary sense, which is well-known to those skilled in the art. Specifically, it refers to a group having a carbon atom directly attached to the remainder of the molecule and having a predominantly hydrocarbon character. Each hydrocarbyl group is independently selected from hydrocarbon substituents, and substituted hydrocarbon substituents containing one or more of halo groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents are present for every ten carbon atoms in the hydrocarbyl group.

As used herein, the term "hydrocarbylene substituent" or "hydrocarbylene group" is used in its ordinary sense, which is well-known to those skilled in the art. Specifically, it refers to a group that is directly attached at two locations of the molecule to the remainder of the molecule by a carbon atom and having predominantly hydrocarbon character. Each hydrocarbylene group is independently selected from divalent hydrocarbon substituents, and substituted divalent hydrocarbon substituents containing halo groups, alkyl groups, aryl groups, alkylaryl groups, arylalkyl groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents is present for every ten carbon atoms in the hydrocarbylene group.

As used herein, the term "percent by weight", unless expressly stated otherwise, means the percentage the recited component represents to the weight of the entire composition.

The terms "soluble," "oil-soluble," or "dispersible" used herein may, but does not necessarily, indicate that the compounds or additives are soluble, dissolvable, miscible, or capable of being suspended in the oil in all proportions. The foregoing terms do mean, however, that they are, for instance, soluble, suspendable, dissolvable, or stably dispersible in oil to an extent sufficient to exert their intended effect in the environment in which the oil is employed. Moreover, the additional incorporation of other additives may also permit incorporation of higher levels of a particular additive, if desired.

The term "TBN" as employed herein is used to denote the Total Base Number in mg KOH/g as measured by the method of ASTM D2896.

The term "lime" as employed herein refers to, for example, calcium hydroxide, calcium oxide, and the like compounds, also known as slaked lime or hydrated lime.

The term "alkyl" as employed herein refers to straight, branched, cyclic, and/or substituted saturated chain moieties of from about 1 to about 100 carbon atoms. The term "alkenyl" as employed herein refers to straight, branched, cyclic, and/or substituted unsaturated chain moieties of from about 3 to about 10 carbon atoms. The term "aryl" as employed herein refers to single and multi-ring aromatic compounds that may include alkyl, alkenyl, alkylaryl, amino, hydroxyl, alkoxy, halo substituents, and/or heteroatoms including, but not limited to, nitrogen, oxygen, and sulfur.

The term "sulfurization ratio" is a weight ratio of sulfurized alkyl phenate to unsulfurized alkyl phenate/unsulfurized alkyl phenol. As discussed more below, the methods herein are effective to form and maintain alkyl phenate additives with high sulfurization ratios. As used herein, when referring to an unsulfurized alkyl phenate or a residual unsulfurized alkyl phenate, both the phenate and phenol forms of the compound are contemplated because the phenate form could readily be acidified to the phenol.

The molecular weight for any embodiment herein may be determined with a gel permeation chromatography (GPC) instrument obtained from Waters or the like instrument and the data processed with Waters Empower Software or the like software. The GPC instrument may be equipped with a Waters Separations Module and Waters Refractive Index detector (or the like optional equipment). The GPC operating conditions may include a guard column, 4 Agilent PLgel columns (length of 300×7.5 mm; particle size of 5μ, and pore size ranging from 100-10000 Å) with the column temperature at about 40° C. Un-stabilized HPLC grade tetrahydrofuran (THF) may be used as solvent, at a flow rate of 1.0 mL/min. The GPC instrument may be calibrated with commercially available polystyrene (PS) standards having a narrow molecular weight distribution ranging from 500-380,000 g/mol. The calibration curve can be extrapolated for samples having a mass less than 500 g/mol. Samples and PS standards can be in dissolved in THF and prepared at concentration of 0.1 to 0.5 wt. % and used without filtration. GPC measurements are also described in U.S. Pat. No. 5,266,223, which is incorporated herein by reference. The GPC method additionally provides molecular weight distribution information; see, for example, W. W. Yau, J. J. Kirkland and D. D. Bly, "Modern Size Exclusion Liquid Chromatography", John Wiley and Sons, New York, 1979, also incorporated herein by reference.

Additional details and advantages of the disclosure will be set forth in part in the description that follows, and/or may be learned by practice of the disclosure. The details and advantages of the disclosure may be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF DRAWING FIGURES

FIG. 1 is a graph of residual or unsulfurized alkyl phenol based on temperature showing the reaction kinetics of regeneration of alkyl phenol during processing.

DETAILED DESCRIPTION

The present disclosure provides a method for preparing a neutral to overbased and sulfurized alkyl phenate product to achieve a high sulfurization ratio of sulfurized alkyl phenate to unsulfurized alkyl phenate in the context of a neutral to an overbased additive, such as one with a TBN of at least about 0, at least about 20, at least about 50, at least about 100 and otherwise about 150 to about 400 as further discussed below. As noted in the background, past attempts at achieving high levels of sulfurization in such context have been met with limited success and have not been able to achieve a sulfurization ratio of about 500:1 or higher (that is, a weight ratio of sulfurized alkyl phenate to unsulfurized alkyl phenate) with such TBN because the high alkalinity and/or processing methods tend to regenerate unsulfurized variants through the manufacturing processing.

In one aspect, the methods herein include first sulfurizing an alkyl phenol with a source of sulfur to provide a sulfurized alkyl phenol. In some approaches, the sulfurization occurs without a base present in the reaction medium. In one approach, the alkyl phenol is derived from an alkylation of a phenol with one or more oligomers obtained from olefins, such as but not limited to, ethylene, propylene, butylene, or mixtures thereof. Next, the sulfurized alkyl phenol is neutralized and optionally overbased in the presence of a solvent to provide a neutral to an overbased and sulfurized alkyl phenate composition. The neutralizing and the optional overbasing is performed at a temperature not exceeding about 140° C. to achieve a sulfurization ratio of about 500:1 or greater in the composition. Lastly, the optionally overbased and sulfurized alkyl phenate composition is subjected to a variety of post-processing steps to obtain the neutral to overbased and sulfurized alkyl phenate product, where all the post processing is conducted at conditions, such as temperatures not to exceed about 140° C., to maintain the sulfurization ratio of about 500:1 or greater. In yet other approaches, the methods herein are effective to achieve sulfurization ratios of the neutral to overbased and sulfurized alkyl phenate product of about 5000:1 to about 500:1, in other approaches, about 4000:1 to about 500:1, in other approaches, about 3500:1 to about 500:1, in other approaches, about 2000:1 to about 500:1, and in yet other approaches, about 5000:1 to about 1000:1, or about 3400:1 to about 1200:1, or even about 2000:1 to about 1000:1. More details of each process step will be described below.

Alkylation of Phenols

The alkyl phenate product of the present disclosure is first obtained through alkylation of a suitable phenol (or hydroxyaromatic) compound with one or more olefins and/or oligomers derived from olefins. Suitable phenol or hydroxyaromatic compounds include monohydroxy and/or polyhydroxy aromatic hydrocarbons having 1 to 4, and in some approaches, 1 to 3, hydroxyl groups. Suitable compounds include but are not limited to phenol, catechol, resorcinol, hydroquinone, pyrogallol, cresol, and the like and mixtures thereof. Preferred starting compounds include phenol.

The alkylating agent includes one or more olefins and/or oligomers derived from olefins selected from ethylene, propylene, butylene, isobutylene, or mixtures thereof. Suitable olefins include isobutylenes, propylene trimers and/or tetramers, butylenes trimers and/or tetramers to suggest but a few examples, but other olefins may be present in the oligomer or alkyl group such as linear olefins, cyclic olefins, branched olefins other than propylene oligomers such as butylene or isobutylene oligomers, arylalkylenes and the like and mixtures thereof. The alkylation may be conducted in the presence of a catalyst such as Lewis acid catalysts, solid acid catalysts, trifluoromethanesulfonic acid, and other acidic molecular sieve catalysts. Exemplary Lewis acid catalysts are known to those of skill and may include aluminum trichloride, aluminum tribromide, aluminum triiodide, boron trifluoride, boron tribromide, boron triiodide and the like. In some approaches, a molar ratio of the phenol or hydroxyaromatic compound to the one or more oligomers may be about 10:1 to about 0.5:1, and in other approaches, about 5:1 to about 2:1. The oligomer alkyl group is commonly attached to the phenol or hydroxyaromatic compound in the ortho and/or para positions, but other substitution may also be present depending on the application.

Sulfurization

The alkyl phenol or alkylhydroxyaromatic compound is next sulfurized by contacting with a sulfur source in a manner effective to achieve a high degree of sulfurization. In approaches, the sulfurization generally introduces sulfur bridging groups between alkyl phenol or alkylhydroxyaromatic moieties. In some approaches, the sulfur bridging is -Sy- groups, wherein y is an integer from 1 to 4 and in other approaches, 1 to 3 and, in some approaches, 1 to 2 and/or with a total sulfur level of up to about 5 percent. The sulfur source may be any suitable sulfur, for example, elemental sulfur or a halide thereof such as sulfur monochloride or sulfur dichloride, hydrogen sulfide, sulfur dioxide and sodium sulfide hydrates. The sulfur can be employed either as molten sulfur or as a solid (powder or particulate) or as a solid suspension in a hydrocarbon liquid. In one approach, the sulfur source is sulfur monochloride, which those of skill appreciate is $S_2Cl_2$, as shown in the reaction Scheme I below. In other approaches, the sulfur source may be a blend of sulfur dichloride ($SCl_2$) and sulfur monochloride ($S_2Cl_2$), and, in particular, a blend of about 60 to about 67 weight percent sulfur dichloride and about 33 to about 40 weight percent of sulfur monochloride. Scheme I illustrates sulfurization at room temperatures (20 to 25° C.) for about 60 minutes using sulfur monochloride (other sulfur sources may be used as well), but other sulfurization conductions may be used as needed for a particular application (such as about 0° C. to about 250° C. for about 1 hour to about 7 hours):

(Scheme I)

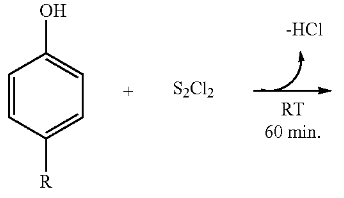

-continued

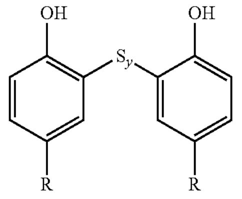

In approaches, the sulfurization occurs in the absence of or devoid of a base, such as sodium hydroxide, potassium hydroxide, or calcium hydroxide, which means less than 1 weight percent base during sulfurization, less than about 0.5 weight percent base, less than about 0.1 weight percent base, or even no base present during sulfurization. Preferably, sulfurization reaction temperatures may be about 0° C. to about 250° C., about 0° C. to about 230° C., about 0° C. to about 120° C., about 40° C. to about 120° C., or about 40° C. to about 60° C. and/or other ranges within such endpoints as needed for a particular application. In some approaches, the sulfur source may be combined with the selected alkyl phenol (optionally in the presence of a solvent) at temperatures ranging from at least about 0° C., at least about 20° C., at least about 40° C., at least about 60° C., at least about 80° C., at least about 100° C. to less than 200° C., less than 180° C., less than about 160° C., less than about 140° C., less than about 120° C., or less than about 100° C. After, the reaction product may be subject to short temperature hold up to about 200° C. for 30 minutes to 60 minutes and/or vacuum strip/distillation at temperatures up to about 200° C. for 30 minutes to 60 minutes as needed for a particular application. The sulfurization process may be for up to about 8 hours, up to about 6 hours, up to about 4 hours, or less depending on the sulfur source. Solvents may be present during the reaction such as heptane, hexane, xylenes, glycols, and the like. When sulfurization occurs first without a base and, in particular, when using sulfur dichloride, the reaction preferentially is driven to high levels of sulfurization, such as intermediate sulfurization ratios of about 500:1 or greater, about 1000:1 or greater, about 2400:1 or greater, and in some approaches, about 5000:1 or less.

In some approaches, a ratio of the sulfur source to the alkyl phenol reactant may be selected to achieve high levels of sulfurization when conducting sulfurization devoid of a base and, in some approaches, to also help maintain low levels of copper corrosion in the final product when used in a lubricant. In one approach, a mol ratio of the sulfur source to the alkyl phenol or alkylhydroxyaromatic reactant in the sulfurization reaction may be about 0.66 or greater and, in other approaches or embodiments, about 0.66 to about 3.5, about 0.67 to about 3.5, about 0.68 to about 3.5, or in yet other approaches or embodiments, about 0.7 to about 3.5, or about 0.7 to about 2.0, or about 0.7 to about 1.4, or even about 0.7 to about 1.0 as needed for a particular application. In other embodiments, a mol ratio of the sulfur source to the alkyl phenol or alkylhydroxyaromatic reactant in the sulfurization reaction may range from at least about 0.66, at least about 0.67, at least about 0.68, at least about 0.69, at least about 0.7, at least about 0.72, at least about 0.74, at least about 0.76, at least about 0.78, or at least about 0.8 to less than about 3.5, less than about 3.0, less than about 2.5, less than about 2.0, less than about 1.5, less than about 1.0. Such mol ratio of the sulfur source to the alkyl phenol reactant helps aid in achieving the high sulfurization ratios of the present disclosure of about 500:1 or greater in the sulfurization reaction (and in other embodiments, about 500:1 to about 5000:1 or about 500:1 to about 4000:1 or about 500:1 to about 3500:1 or about 500:1 to about 2000:1), and in some approaches, allow later processing steps as described below to maintain or increase sulfurization ratios such that the final sulfurized and overbased alkyl phenate product maintains a high sulfurization ratio of sulfurized to unsulfurized phenate. In other approaches or embodiments, such mol ratios herein of the sulfur source to the alkyl phenol may aid in achieving sulfurization ratios ranging from at least about 500:1, at least about 600:1, at least about 700:1, at least about 800:1, at least about 900:1, at least about 1000:1, at least about 1100:1 or at least about 1200:1 to about 5000:1 or less, about 4500:1 or less, about 4000:1 or less, about 3500:1 or less, about 3000:1 or less, about 2500:1 or less, or about 2000:1 or less. In other embodiments, the mol ratios and resultant sulfurization ratios herein may also include any other ranges within the noted endpoints as needed for a particular application. In yet other approaches, the mol ratios of the sulfur source to the alkyl phenol may aid in achieving residual unsulfurized alkyl phenate and/or unsulfurized alkyl phenol of about 0.2 weight percent or less, about 0.1 weight percent or less, about 0.08 weight percent or less, about 0.06 weight percent or less, about 0.04 weight percent or less, or about 0.03 weight percent or less or, in some approaches, undetectable amounts.

Due to the high sulfurization ratios, the methods herein are such that any residual unsulfurized alkyl phenol need not be removed after the sulfurization and/or after any of the next process steps, such as the neutralizing, overbasing, and/or post processing. The methods herein, rather, minimize the generation and/or regeneration of any unsulfurized variants and, thus, avoid the need to remove such undesired component.

Neutralization

After the sulfurization, the sulfurized alkyl phenol or sulfurized alkylhydroxyaromatic compound with the already achieved high sulfurization ratio is then neutralized to provide a phenate or salt of the sulfurized alkyl phenol or alkylhydroxyaromatic compound. In one approach, neutralization is performed by contacting the sulfurized alkyl phenol with a metal base under reactive conditions, in some approaches, in a liquid hydrocarbon diluent with a promotor to provide a phenate or salt of the sulfurized alkylhydroxyaromatic compound. In some instances, the reaction can be conducted under an inert gas, such as nitrogen. The metal base may be added either in a single addition or in multiple additions at various times during the reaction if needed for certain applications. Neutralization may occur via the exemplary reaction Scheme II shown below, but other reactions may proceed as needed depending on the application, materials, and conditions.

(Scheme II)

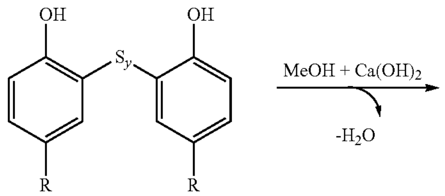

-continued

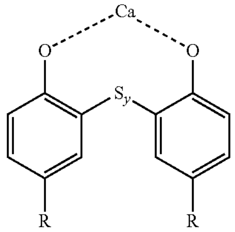

Exemplary metal base reactants include hydroxides, oxides, or alkoxides of a metal such as but not limited to an alkali metal salt derived from a metal base selected from an alkali hydroxide, alkali oxide or an alkali alkoxide, or an alkaline earth metal salt derived from a metal base selected from an alkaline earth hydroxide, alkaline earth oxide or alkaline earth alkoxide. Suitable metal base compounds include lithium hydroxide, potassium hydroxide, sodium hydroxide, magnesium hydroxide, calcium hydroxide, barium hydroxide and aluminum hydroxide. Other examples of metal basic compounds include lithium oxide, magnesium oxide, calcium oxide and barium oxide. In a preferred example, the alkaline earth metal base is lime or calcium hydroxide. Additives may be borated as needed depending on the application and use.

Neutralization (and subsequent overbasing discussed more below) is conducted in the presence of a solvent or solvent system. In one approach, the solvent and/or system is one or more organic compounds having a boiling point of less than about 100° C. and, in other approaches, compounds having a boiling point less than about 100° C. at about 1000 to about 40 mbars of pressure (in other approaches, about 1000 to about 300 mbar). Suitable examples include xylene, toluene, octane, butanol, heptane, methanol, pentanol, acetone, benzene, cyclohexane, cyclopentane, ethanol, hexane, pentane, propanol, water, or combinations thereof. In one approach, solvents include one or more of heptane, methanol, water, and combinations thereof and, in one approach, the solvent system for neutralization may be about 80 to about 95 weight percent heptane, about 2 to about 10 weight percent methanol, and about 5 to about 15 weight percent water based on the total amount of solvent. In another approach, the solvent may be a heptane/methanol system and include, in some embodiments, about 85 to about 95 percent heptane and about 5 to about 15 percent methanol. The total amount of solvent for neutralization may be about 10 to about 80 weight percent based on the total weight of solvent, base, and alkyl phenol/phenate. In one approach, the source of alkali and/or alkaline earth metal may be added in excess as a slurry (such as, a pre-mixture of metal base and solvent) and then reacted with the sulfurized alkyl phenol compound.

In one approach, the neutralization solvent is devoid of materials with a higher boiling point, such as solvents having a boiling point of about 100° C. or higher at the noted pressures such as ethylene glycol propylene glycol, and/or decanol and the like solvents. In optional approaches and as used herein, devoid or free of such compounds means the solvent has less than about 10 weight percent, less than about 5 weight percent, less than about 2 weight percent, less than 1 weight percent, less than 0.5 weight percent, or none of the noted high boiling solvents.

The neutralization reaction between the metal base and the sulfurized alkyl phenol is conducted at conditions effective to maintain the high sulfurization ratios achieved during the sulfurization reactions. In one approach, neutralization occurs at low temperatures, such as temperatures no greater than about 140° C., in some approaches, no greater than about 120° C., in other approaches, no greater than about 100° C., and in yet preferred approaches, at temperatures no greater than about 80° C. in order to maintain the high sulfurization ratios achieved during the prior sulfurization reactions. Conducting neutralization at higher temperatures tends to result in increased levels and/or regeneration of unsulfurized alkyl phenols or alkyl phenates that reduce the sulfurization ratio, which is undesired. Rather, the methods herein select conditions to maintain the high sulfurization levels and ratios throughout processing. In other approaches, neutralization is conducted at a temperatures ranging from at least about 20° C., at least about 30° C., at least about 40° C., at least about 50° C., at least about 60° C. to less than about 140° C., less than about 130° C., less than about 120° C., less than about 110° C., less than about 100° C., less than about 90° C., or less than about 80° C. The neutralization reaction should occur for about 5 to about 60 min.

Overbasing

Next, overbasing is optional, but preferred in some embodiments, and conducted either during or, alternatively, after the neutralization. In one approach, the sulfurized alkyl phenol/alkyl phenate is overbased by reacting with an excess of the metal base and/or reacting with an acidic overbasing compound such as, for example, carbon dioxide or boric acid. In one approach, overbasing is via carbonation (a reaction with carbon dioxide) in the presence of solvent, such as any of the solvents from the solvent system described above with the neutralization. One convenient carbonation reaction is passing gaseous carbon dioxide through the reaction mixture. Excess solvents and any water formed during the overbasing reaction can be removed as needed by distillation either during or after the reaction as discussed further below.

In one embodiment, an exemplary overbasing reaction may be reacting the sulfurized alkyl phenol or salt thereof with an alkali or alkaline earth metal such as lime in the presence of carbon dioxide and the solvent system as already discussed above. Conveniently, the reaction may be conducted by bubbling gaseous carbon dioxide through the reaction and solvent system mixture. Just as the temperature of the neutralization is controlled at low levels to maintain the high sulfurization levels, the temperature of overbasing is also kept low to maintain the high sulfurization levels and ratios throughout the overbasing. For instance, overbasing temperatures are also no greater than about 140° C., in some approaches, no greater than about 120° C., in other approaches, no greater than about 100° C., and in yet preferred approaches, at temperatures no greater than about 80° C. in order to maintain the high sulfurization ratios from the sulfurization and neutralization during the overbasing processing. Conducting overbasing at higher temperatures also tends to result in higher levels of or increased regeneration of residual unsulfurized alkyl phenols/phenate leading to a reduction in the sulfurization ratio, which is undesired.

In other approaches, overbasing is also conducted at a temperatures ranging from at least about 20° C., at least about 30° C., at least about 40° C., at least about 50° C., at least about 60° C. to less than about 140° C., less than about 130° C., less than about 120° C., less than about 110° C., less than about 100° C., less than about 90° C., or less than about 80° C. The degree of overbasing may be controlled by the quantity of the alkali or alkaline earth metal, amount of carbon dioxide and other reactants (if any) added to the reaction mixture as well as the reaction conditions used during the carbonation process. In approaches, overbasing or overbasing via carbonation occurs for a time sufficient to achieve a desired degree of overbasing or TBN and, in some approaches, may be about 30 minutes to about 180 minutes at the noted temperatures.

After the overbasing, the overbased and sulfurized alkyl phenate may have a TBN of about 100 to about 400, or about 150 to about 400, and in other approaches, about 200 to about 300, and in yet other approaches, about 220 to about 275. Even when overbased, the sulfurized alkyl phenate maintains a high level of sulfurization compared to unsulfurized alkyl phenate or alkyl phenol, and this sulfurization ratio is maintained at least about 500:1 after the overbasing step and as further discussed below during post processing.

Post Processing

After the optional overbasing, the composition including the sulfurized alkyl phenate is often subjected to a number of steps to prepare a final sulfurized alkyl phenate product. However, such post processing steps also should be conducted using conditions effective to maintain the high sulfurization ratio. In approaches, all post-processing is conducted a low temperature in order to maintain the high levels of sulfurization relative to unsulfurized alkyl phenate and to not regenerate unsulfurized alkyl phenol or phenate.

Examples of post processing that occurs at low temperatures include one or more of vacuum stripping, distillation, sparging, filtering, degassing, evaporation, wiped-film evaporating, centrifuging, diluting, liquid-liquid extraction, membrane separation, chromatography, absorption, supercritical extractions, and/or combinations thereof and wherein all post processing individually and/or combined is conducted at conditions effective to maintain the high sulfurization levels, such as at a low temperature not to exceed about 140° C. Similar to the neutralization and overbasing, any post processing is also conducted at a temperature ranging from at least about 20° C., at least about 30° C., at least about 40° C., at least about 50° C., at least about 60° C. to less than about 140° C., less than about 130° C., less than about 120° C., less than about 110° C., less than about 100° C., less than about 90° C., or less than about 80° C.

The method steps herein produce an overbased and sulfurized alkyl phenate product that has a high level of sulfurization or a high sulfurization ratio of sulfurized to unsulfurized alkyl phenate/alkyl phenol of at least about 500:1 and, in other approaches, about 500:1 to about 5000:1 and, in yet other approaches, about 1000:1 to about 5000:1, about 1000:1 to about 3500:1, or even about 1000:1 to about 2000:1 evidencing a high level of sulfurized alkyl phenate, when in neutral to overbased form, relative to unsulfurized alkyl phenate or unsulfurized alkyl phenol. In other approaches, the additives and methods herein have less than about 0.2 weight percent, less than about 0.1 weight percent, less than about 0.08 weight percent, less than about 0.05 weight percent, or less than about 0.03 weight percent of unsulfurized alkyl phenates/alkyl phenols or about 0.01 to about 0.2 weight percent or any range therein of the unsulfurized alkyl phenate/alkyl phenols.

Unique to the methods herein is that unsulfurized alkyl phenate or alkyl phenols generally do not need to be removed (such as after sulfurization or after any intermediate step) because the method steps do not generate and/or do not regenerate unsulfurized alkyl phenate or alkyl phenols within any of the various process steps, and rather, maintain the high levels of sulfurization throughout processing. As such, the methods herein, therefore, avoid the expense and complexity of prior methods that necessitated the removal of residual and/or unsulfurized alkyl phenate/phenols either intermediate to the process or during post-processing steps.

Lubricating Oil Compositions

The optionally overbased and sulfurized alkyl phenate products described herein may be combined with a major amount of a base oil blend or base oil blend of lubricating viscosity (as described below) in combination with one or more further optional additives to produce a lubricating oil composition. In approaches, the lubricating oil compositions includes about 50 weight percent or more of the base oil, about 60 weight percent or more, about 70 weight percent or more, or about 80 weight percent or more to about 95 weight percent or less, about 90 weight percent or less, about 85 weight percent or less of the base oil as further discussed below.

In approaches, the lubricating oil compositions herein may include about 0.02 to about 5 weight percent of the optionally overbased and sulfurized alkyl phenate product, in other approaches, about 0.2 to about 3 weight percent, and in yet other approaches, about 0.2 to about 2 weight percent in a base oil or base oil blend.

In some approaches, the additives herein can be used as detergents in lubricating oils to neutralize acids and/or to help control rust, corrosion, and deposits. In addition, the detergents described herein may also be used in fuels, including but not limited to, gasoline, diesel, biodiesel, for spark, compression, and hybrid engines.

Lubricants, combinations of components, dispersant inhibitor packages, and/or individual components of the present description may be suitable for use in various types of lubricants such as automotive lubricants and/or greases, internal combustion engine oils, hybrid engine oils, hybrid engine oils, electric engine lubricants, drivetrain lubricants, transmission lubricants, gear oils, hydraulic lubricants, tractor hydraulic fluids, metalworking fluids, turbine engine lubricants, stationary engine lubricants, tractor lubricants, motorcycle lubricants, power steering fluids, clutch fluids, axle fluids, wet break fluids, and the like.

Suitable engine types may include, but are not limited to heavy-duty diesel, passenger car, light duty diesel, medium speed diesel, or marine engines. An internal combustion engine may be a diesel fueled engine, a gasoline fueled engine, a natural gas fueled engine, a bio-fueled engine, a mixed diesel/biofuel fueled engine, a mixed gasoline/biofuel fueled engine, an alcohol fueled engine, a mixed gasoline/alcohol fueled engine, a compressed natural gas (CNG) fueled engine, or mixtures thereof. A diesel engine may be a compression-ignited engine. A gasoline engine may be a spark-ignited engine. An internal combustion engine may also be used in combination with an electrical or battery source of power. An engine so configured is commonly known as a hybrid engine. The internal combustion engine may be a 2-stroke, 4-stroke, or rotary engine. Suitable internal combustion engines include marine diesel engines (such as inland marine), aviation piston engines, low-load diesel engines, and motorcycle, automobile, locomotive, and truck engines. Engines may be coupled with a turbocharger.

The lubricating oil composition for an internal combustion engine may be suitable for any engine lubricant irrespective of the sulfur, phosphorus, or sulfated ash (ASTM D-874) content. The sulfur content of the engine oil lubricant may be about 1 wt % or less, or about 0.8 wt % or less, or about 0.5 wt % or less, or about 0.3 wt % or less, or about 0.2 wt % or less. In one embodiment the sulfur content may be in the range of about 0.001 wt % to about 0.5 wt %, or about 0.01 wt % to about 0.3 wt %. The phosphorus content may be about 0.2 wt % or less, or about 0.1 wt % or less, or about 0.085 wt % or less, or about 0.08 wt % or less, or even about 0.06 wt % or less, about 0.055 wt % or less, or about 0.05 wt % or less. In one embodiment, the phosphorus content may be about 50 ppm to about 1000 ppm, or about 325 ppm to about 850 ppm. The total sulfated ash content may be about 2 wt % or less, or about 1.5 wt % or less, or about 1.1 wt % or less, or about 1 wt % or less, or about 0.8 wt % or less, or about 0.5 wt % or less. In one embodiment the sulfated ash content may be about 0.05 wt % to about 0.9 wt %, or about 0.1 wt % or about 0.2 wt % to about 0.45 wt %. In another embodiment, the sulfur content may be about 0.4 wt % or less, the phosphorus content may be about 0.08 wt % or less, and the sulfated ash is about 1 wt % or less. In yet another embodiment the sulfur content may be about 0.3 wt % or less, the phosphorus content is about 0.05 wt % or less, and the sulfated ash may be about 0.8 wt % or less.

Further, lubricants of the present description may be suitable to meet one or more industry specification requirements such as ILSAC GF-3, GF-4, GF-5, GF-6, PC-11, CF, CF-4, CH-4, CK-4, FA-4, CJ-4, CI-4 Plus, CI-4, API SG, SJ, SL, SM, SN, SN PLUS, ACEA A1/B1, A2/B2, A3/B3, A3/B4, A5/B5, C1, C2, C3, C4, C5, E4/E6/E7/E9, Euro 5/6, JASO DL-1, Low SAPS, Mid SAPS, or original equipment manufacturer specifications such as Dexos1™, Dexos2™, MB-Approval 229.1, 229.3, 229.5, 229.51/229.31, 229.52, 229.6, 229.71, 226.5, 226.51, 228.0/.1, 228.2/.3, 228.31, 228.5, 228.51, 228.61, VW 501.01, 502.00, 503.00/503.01, 504.00, 505.00, 505.01, 506.00/506.01, 507.00, 508.00, 509.00, 508.88, 509.99, BMW Longlife-01, Longlife-01 FE, Longlife-04, Longlife-12 FE, Longlife-14 FE+, Longlife-17 FE+, Porsche A40, C30, Peugeot Citroën Automobiles B71 2290, B71 2294, B71 2295, B71 2296, B71 2297, B71 2300, B71 2302, B71 2312, B71 2007, B71 2008, Renault RN0700, RN0710, RN0720, Ford WSS-M2C153-H, WSS-M2C930-A, WSS-M2C945-A, WSS-M2C913A, WSS-M2C913-B, WSS-M2C913-C, WSS-M2C913-D, WSS-M2C948-B, WSS-M2C948-A, GM 6094-M, Chrysler MS-6395, Fiat 9.55535 G1, G2, M2, N1, N2, Z2, S1, S2, S3, S4, T2, DS1, DSX, GH2, GS1, GSX, CR1, Jaguar Land Rover STJLR.03.5003, STJLR.03.5004, STJLR.03.5005, STJLR.03.5006, STJLR.03.5007, STJLR.51.5122 or any past or future PCMO or HDD specifications not mentioned herein. In some embodiments for passenger car motor oil (PCMO) applications, the amount of phosphorus in the finished fluid is 1000 ppm or less or 900 ppm or less or 800 ppm or less.

Base Oil or Base Oil Blend: The base oil used in the lubricating oil compositions herein may be oils of lubricating viscosity and selected from any of the base oils in Groups I-V as specified in the American Petroleum Institute (API) Base Oil Interchangeability Guidelines. The five base oil groups are generally set forth in Table 1 below:

TABLE 1

| Base oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | All polyalphaolefins (PAOs) | | | |
| Group V | All others not included in Groups I, II, III, or IV | | | |

Groups I, II, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may be referred to as synthetic fluids in the industry. Group II+ may comprise high viscosity index Group II.

The base oil blend used in the disclosed lubricating oil composition may be a mineral oil, animal oil, vegetable oil, synthetic oil, synthetic oil blends, or mixtures thereof. Suitable oils may be derived from hydrocracking, hydrogenation, hydrofinishing, unrefined, refined, and re-refined oils, and mixtures thereof.

Unrefined oils are those derived from a natural, mineral, or synthetic source without or with little further purification treatment. Refined oils are similar to the unrefined oils except that they have been treated in one or more purification steps, which may result in the improvement of one or more properties. Examples of suitable purification techniques are solvent extraction, secondary distillation, acid or base extraction, filtration, percolation, and the like. Oils refined to the quality of an edible may or may not be useful. Edible oils may also be called white oils. In some embodiments, lubricating oil compositions are free of edible or white oils.

Re-refined oils are also known as reclaimed or reprocessed oils. These oils are obtained similarly to refined oils using the same or similar processes. Often these oils are additionally processed by techniques directed to removal of spent additives and oil breakdown products.

Mineral oils may include oils obtained by drilling or from plants and animals or any mixtures thereof. For example such oils may include, but are not limited to, castor oil, lard oil, olive oil, peanut oil, corn oil, soybean oil, and linseed oil, as well as mineral lubricating oils, such as liquid petroleum oils and solvent-treated or acid-treated mineral lubricating oils of the paraffinic, naphthenic or mixed paraffinic-naphthenic types. Such oils may be partially or fully hydrogenated, if desired. Oils derived from coal or shale may also be useful.

Useful synthetic lubricating oils may include hydrocarbon oils such as polymerized, oligomerized, or interpolymerized olefins (e.g., polybutylenes, polypropylenes, propyleneisobutylene copolymers); poly(1-hexenes), poly(1-octenes), trimers or oligomers of 1-decene, e.g., poly(1-decenes), such materials being often referred to as $\alpha$-olefins, and mixtures thereof; alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulfides and the derivatives, analogs and homologs thereof or mixtures thereof. Polyalphaolefins are typically hydrogenated materials.

Other synthetic lubricating oils include polyol esters, diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerized Fischer-Tropsch hydrocarbons or waxes. In one embodiment oils may be prepared by a Fischer-Tropsch gas-to-liquid synthetic procedure as well as other gas-to-liquid oils.

The major amount of base oil included in a lubricating composition may be selected from the group consisting of Group I, Group II, a Group III, a Group IV, a Group V, and a combination of two or more of the foregoing, and wherein the major amount of base oil is other than base oils that arise from provision of additive components or viscosity index improvers in the composition. In another embodiment, the major amount of base oil included in a lubricating composition may be selected from the group consisting of Group II, a Group III, a Group IV, a Group V, and a combination of two or more of the foregoing, and wherein the major amount of base oil is other than base oils that arise from provision of additive components or viscosity index improvers in the composition.

The amount of the oil of lubricating viscosity present may be the balance remaining after subtracting from 100 wt % the sum of the amount of the performance additives inclusive of viscosity index improver(s) and/or pour point depressant(s) and/or other top treat additives. For example, the oil of lubricating viscosity that may be present in a finished fluid may be a major amount, such as greater than about 50 wt %, greater than about 60 wt %, greater than about 70 wt %, greater than about 80 wt %, greater than about 85 wt %, or greater than about 90 wt %.

Optional Additives:

The lubricating oil compositions herein may also include a number of optional additives combined with the optionally overbased and sulfurized alkyl phenate product as needed to meet performance standards. Those optional additives are described in the following paragraphs.

Dispersants: The lubricating oil composition may optionally include one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless type dispersants are characterized by a polar group attached to a relatively high molecular weight hydrocarbon chain. Typical ashless dispersants include N-substituted long chain alkenyl succinimides. Examples of N-substituted long chain alkenyl succinimides include polyisobutylene succinimide with the number average molecular weight of the polyisobutylene substituent being in the range about 350 to about 50,000, or to about 5,000, or to about 3,000, as measured by GPC. Succinimide dispersants and their preparation are disclosed, for instance in U.S. Pat. No. 7,897,696 or U.S. Pat. No. 4,234,435. The alkenyl substituent may be prepared from polymerizable monomers containing about 2 to about 16, or about 2 to about 8, or about 2 to about 6 carbon atoms. Succinimide dispersants are typically the imide formed from a polyamine, typically a poly(ethyleneamine).

Preferred amines are selected from polyamines and hydroxyamines. Examples of polyamines that may be used include, but are not limited to, diethylene triamine (DETA), triethylene tetramine (TETA), tetraethylene pentamine (TEPA), and higher homologues such as pentaethylamine hexamine (PEHA), and the like.

A suitable heavy polyamine is a mixture of polyalkylene-polyamines comprising small amounts of lower polyamine oligomers such as TEPA and PEHA (pentaethylene hexamine) but primarily oligomers with 6 or more nitrogen atoms, 2 or more primary amines per molecule, and more extensive branching than conventional polyamine mixtures. A heavy polyamine preferably includes polyamine oligomers containing 7 or more nitrogens per molecule and with 2 or more primary amines per molecule. The heavy polyamine comprises more than 28 wt. % (e.g. >32 wt. %) total nitrogen and an equivalent weight of primary amine groups of 120-160 grams per equivalent.

In some approaches, suitable polyamines are commonly known as PAM and contain a mixture of ethylene amines where TEPA and pentaethylene hexamine (PEHA) are the major part of the polyamine, usually less than about 80%.

Typically, PAM has 8.7-8.9 milliequivalents of primary amine per gram (an equivalent weight of 115 to 112 grams per equivalent of primary amine) and a total nitrogen content of about 33-34 wt. %. Heavier cuts of PAM oligomers with practically no TEPA and only very small amounts of PEHA but containing primarily oligomers with more than 6 nitrogens and more extensive branching, may produce dispersants with improved dispersancy.

In an embodiment the present disclosure further comprises at least one polyisobutylene succinimide dispersant derived from polyisobutylene with a number average molecular weight in the range about 350 to about 50,000, or to about 5000, or to about 3000, as determined by GPC. The polyisobutylene succinimide may be used alone or in combination with other dispersants.

In some embodiments, polyisobutylene, when included, may have greater than 50 mol %, greater than 60 mol %, greater than 70 mol %, greater than 80 mol %, or greater than 90 mol % content of terminal double bonds. Such PIB is also referred to as highly reactive PIB ("HR-PIB"). HR-PIB having a number average molecular weight ranging from about 800 to about 5000, as determined by GPC, is suitable for use in embodiments of the present disclosure. Conventional PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable, as determined by GPC. Such HR-PIB is commercially available, or can be synthesized by the polymerization of isobutene in the presence of a non-chlorinated catalyst such as boron trifluoride, as described in U.S. Pat. No. 4,152,499 to Boerzel, et al. and U.S. Pat. No. 5,739,355 to Gateau, et al. When used in the aforementioned thermal ene reaction, HR-PIB may lead to higher conversion rates in the reaction, as well as lower amounts of sediment formation, due to increased reactivity. A suitable method is described in U.S. Pat. No. 7,897,696.

In one embodiment, the present disclosure further comprises at least one dispersant derived from polyisobutylene succinic anhydride ("PIBSA"). The PIBSA may have an average of between about 1.0 and about 2.0 succinic acid moieties per polymer.

The % actives of the alkenyl or alkyl succinic anhydride can be determined using a chromatographic technique. This method is described in column 5 and 6 in U.S. Pat. No. 5,334,321.

The percent conversion of the polyolefin is calculated from the % actives using the equation in column 5 and 6 in U.S. Pat. No. 5,334,321.

Unless stated otherwise, all percentages are in weight percent and all molecular weights are number average molecular weights determined by gel permeation chromatography (GPC) using commercially available polystyrene standards (with a number average molecular weight of 180 to about 18,000 as the calibration reference).

In one embodiment, the dispersant may be derived from a polyalphaolefin (PAO) succinic anhydride. In one embodiment, the dispersant may be derived from olefin maleic anhydride copolymer. As an example, the dispersant may be described as a poly-PIBSA. In an embodiment, the dispersant may be derived from an anhydride which is grafted to an ethylene-propylene copolymer.

A suitable class of nitrogen-containing dispersants may be derived from olefin copolymers (OCP), more specifically, ethylene-propylene dispersants which may be grafted with maleic anhydride. A more complete list of nitrogen-containing compounds that can be reacted with the functionalized OCP are described in U.S. Pat. Nos. 7,485,603; 7,786,057; 7,253,231; 6,107,257; and 5,075,383; and/or are commercially available.

One class of suitable dispersants may also be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may also be high molecular weight esters or half ester amides. A suitable dispersant may also be post-treated by conventional methods by a reaction with any of a variety of agents. Among these are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. Nos. 7,645,726; 7,214,649; and 8,048,831 are incorporated herein by reference in their entireties.

In addition to the carbonate and boric acids post-treatments both the compounds may be post-treated, or further post-treatment, with a variety of post-treatments designed to improve or impart different properties. Such post-treatments include those summarized in columns 27-29 of U.S. Pat. No. 5,241,003, hereby incorporated by reference. Such treatments include, treatment with: Inorganic phosphorous acids or anhydrates (e.g., U.S. Pat. Nos. 3,403,102 and 4,648,980); Organic phosphorous compounds (e.g., U.S. Pat. No. 3,502,677); Phosphorous pentasulfides; Boron compounds as already noted above (e.g., U.S. Pat. Nos. 3,178,663 and 4,652,387); Carboxylic acid, polycarboxylic acids, anhydrides and/or acid halides (e.g., U.S. Pat. Nos. 3,708,522 and 4,948,386); Epoxides polyepoxiates or thioexpoxides (e.g., U.S. Pat. Nos. 3,859,318 and 5,026,495); Aldehyde or ketone (e.g., U.S. Pat. No. 3,458,530); Carbon disulfide (e.g., U.S. Pat. No. 3,256,185); Glycidol (e.g., U.S. Pat. No. 4,617,137); Urea, thiourea or guanidine (e.g., U.S. Pat. Nos. 3,312,619; 3,865,813; and British Patent GB 1,065,595); Organic sulfonic acid (e.g., U.S. Pat. No. 3,189,544 and British Patent GB 2,140,811); Alkenyl cyanide (e.g., U.S. Pat. Nos. 3,278,550 and 3,366,569); Diketene (e.g., U.S. Pat. No. 3,546,243); A diisocyanate (e.g., U.S. Pat. No. 3,573,205); Alkane sultone (e.g., U.S. Pat. No. 3,749,695); 1,3-Dicarbonyl Compound (e.g., U.S. Pat. No. 4,579,675); Sulfate of alkoxylated alcohol or phenol (e.g., U.S. Pat. No. 3,954,639); Cyclic lactone (e.g., U.S. Pat. Nos. 4,617,138; 4,645,515; 4,668,246; 4,963,275; and 4,971,711); Cyclic carbonate or thiocarbonate linear monocarbonate or polycarbonate, or chloroformate (e.g., U.S. Pat. Nos. 4,612,132; 4,647,390; 4,648,886; 4,670,170); Nitrogen-containing carboxylic acid (e.g., U.S. Pat. No. 4,971,598 and British Patent GB 2,140,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603 and 4,666,460); Cyclic carbonate or thiocarbonate, linear monocarbonate or polycarbonate, or chloroformate (e.g., U.S. Pat. Nos. 4,612,132; 4,647,390; 4,646,860; and 4,670,170); Nitrogen-containing carboxylic acid (e.g., U.S. Pat. No. 4,971,598 and British Patent GB 2,440,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603, and 4,666,460); Cyclic carbamate, cyclic thiocarbamate or cyclic dithiocarbamate (e.g., U.S. Pat. Nos. 4,663,062 and 4,666,459); Hydroxyaliphatic carboxylic acid (e.g., U.S. Pat. Nos. 4,482,464; 4,521,318; 4,713,189); Oxidizing agent (e.g., U.S. Pat. No. 4,379,064); Combination of phosphorus pentasulfide and a polyalkylene polyamine (e.g., U.S. Pat. No. 3,185,647); Combination of carboxylic acid or an aldehyde or ketone and sulfur or sulfur chloride (e.g., U.S. Pat. Nos. 3,390,086; 3,470,098); Combination of a hydrazine and carbon disulfide (e.g. U.S. Pat. No. 3,519,564); Combination of an aldehyde and a phenol (e.g., U.S. Pat. Nos. 3,649,229; 5,030,249; 5,039,307); Combination of an aldehyde and an O-diester of dithiophosphoric acid (e.g., U.S. Pat. No. 3,865,740); Combination of a hydroxyaliphatic carboxylic acid and a boric acid (e.g., U.S. Pat. No. 4,554,086); Combination of a hydroxyaliphatic carboxylic acid, then formaldehyde and a phenol (e.g., U.S. Pat. No. 4,636,322); Combination of a hydroxyaliphatic carboxylic acid and then an aliphatic dicarboxylic acid (e.g., U.S. Pat. No. 4,663,064); Combination of formaldehyde and a phenol and then glycolic acid (e.g., U.S. Pat. No. 4,699,724); Combination of a hydroxyaliphatic carboxylic acid or oxalic acid and then a diisocyanate (e.g. U.S. Pat. No. 4,713,191); Combination of inorganic acid or anhydride of phosphorus or a partial or total sulfur analog thereof and a boron compound (e.g., U.S. Pat. No. 4,857,214); Combination of an organic diacid then an unsaturated fatty acid and then a nitrosoaromatic amine optionally followed by a boron compound and then a glycolating agent (e.g., U.S. Pat. No. 4,973,412); Combination of an aldehyde and a triazole (e.g., U.S. Pat. No. 4,963,278); Combination of an aldehyde and a triazole then a boron compound (e.g., U.S. Pat. No. 4,981,492); Combination of cyclic lactone and a boron compound (e.g., U.S. Pat. Nos. 4,963,275 and 4,971,711). The above-mentioned patents are herein incorporated in their entireties.

The TBN of a suitable dispersant may be from about 10 to about 65 mg KOH/g dispersant, on an oil-free basis, which is comparable to about 5 to about 30 TBN if measured on a dispersant sample containing about 50% diluent oil. TBN is measured by the method of ASTM D2896.

In yet other embodiments, the optional dispersant additive may be a hydrocarbyl substituted succinamide or succinimide dispersant. In approaches, the hydrocarbyl substituted succinamide or succinimide dispersant may be derived from a hydrocarbyl substituted acylating agent reacted with a polyalkylene polyamine and wherein the hydrocarbyl substituent of the succinamide or the succinimide dispersant is a linear or branched hydrocarbyl group having a number average molecular weight of about 250 to about 5,000 as measured by GPC using polystyrene as a calibration reference.

In some approaches, the polyalkylene polyamine used to form the dispersant has the Formula

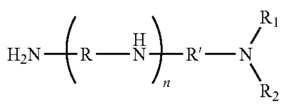

wherein each R and R', independently, is a divalent C1 to C6 alkylene linker, each $R_1$ and $R_2$, independently, is hydrogen, a C1 to C6 alkyl group, or together with the nitrogen atom to which they are attached form a 5- or 6-membered ring optionally fused with one or more aromatic or non-aromatic rings, and n is an integer from 0 to 8. In other approaches, the polyalkylene polyamine is selected from the group consisting of a mixture of polyethylene polyamines having an average of 5 to 7 nitrogen atoms, triethylenetetramine, tetraethylenepentamine, and combinations thereof.

The dispersant, if present, can be used in an amount sufficient to provide up to about 20 wt %, based upon the final weight of the lubricating oil composition. Another amount of the dispersant that can be used may be about 0.1 wt % to about 15 wt %, or about 0.1 wt % to about 10 wt %, about 0.1 to 8 wt %, or about 1 wt % to about 10 wt %, or about 1 wt % to about 8 wt %, or about 1 wt % to about 6 wt %, based upon the final weight of the lubricating oil composition. In some embodiments, the lubricating oil composition utilizes a mixed dispersant system. A single type or a mixture of two or more types of dispersants in any desired ratio may be used.

Antioxidants: The lubricating oil compositions herein also may optionally contain one or more antioxidants. Antioxidant compounds are known and include for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. Antioxidant compounds may be used alone or in combination.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 available from BASF or an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms. Another commercially available hindered phenol antioxidant may be an ester and may include Ethanox™ 4716 available from Albemarle Corporation.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight, based upon the final weight of the lubricating oil composition. In an embodiment, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In one embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

In another alternative embodiment the antioxidant composition also contains a molybdenum-containing antioxidant in addition to the phenolic and/or aminic antioxidants discussed above. When a combination of these three antioxidants is used, preferably the ratio of phenolic to aminic to molybdenum-containing is (0 to 2):(0 to 2):(0 to 1).

The one or more antioxidant(s) may be present in ranges about 0 wt % to about 20 wt %, or about 0.1 wt % to about 10 wt %, or about 1 wt % to about 5 wt %, of the lubricating oil composition.

Antiwear Agents: The lubricating oil compositions herein also may optionally contain one or more antiwear agents. Examples of suitable antiwear agents include, but are not limited to, a metal thiophosphate; a metal dialkyldithiophosphate; a phosphoric acid ester or salt thereof; a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. A suitable antiwear agent may be a molybdenum dithiocarbamate. The phosphorus containing antiwear agents are more fully described in European Patent 612 839. The metal in the dialkyl dithio phosphate salts may be an alkali metal, alkaline earth metal, aluminum, lead, tin, molybdenum, manganese, nickel, copper, titanium, or zinc. A useful antiwear agent may be zinc dialkyldithiophosphate.

Further examples of suitable antiwear agents include titanium compounds, tartrates, tartrimides, oil soluble amine salts of phosphorus compounds, sulfurized olefins, phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulfides. The tartrate or tartrimide may contain alkyl-ester groups, where the sum of carbon atoms on the alkyl groups may be at least 8. The antiwear agent may in one embodiment include a citrate.

The antiwear agent may be present in ranges including about 0 wt % to about 15 wt %, or about 0.01 wt % to about 10 wt %, or about 0.05 wt % to about 5 wt %, or about 0.1 wt % to about 3 wt % of the lubricating oil composition.

Boron-Containing Compounds: The lubricating oil compositions herein may optionally contain one or more boron-containing compounds. Examples of boron-containing compounds include borate esters, borated fatty amines, borated epoxides, borated detergents, and borated dispersants, such as borated succinimide dispersants, as disclosed in U.S. Pat. No. 5,883,057. The boron-containing compound, if present, can be used in an amount sufficient to provide up to about 8 wt %, about 0.01 wt % to about 7 wt %, about 0.05 wt % to about 5 wt %, or about 0.1 wt % to about 3 wt % of the lubricating oil composition.

Additional Detergents: The lubricating oil composition may optionally further comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds, or methylene bridged phenols. Suitable detergents and their methods of preparation are described in greater detail in numerous patent publications, including U.S. Pat. No. 7,732,390 and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. In some embodiments, a detergent may contain traces of other metals such as magnesium or calcium in amounts such as 50 ppm or less, 40 ppm or less, 30 ppm or less, 20 ppm or less, or 10 ppm or less. A suitable detergent may include alkali or alkaline earth metal salts of petroleum sulfonic acids and long chain mono- or di-alkylarylsulfonic acids with the aryl group being benzyl, tolyl, and xylyl. Examples of suitable detergents include, but are not limited to, calcium phenates, calcium sulfur containing phenates, calcium sulfonates, calcium calixarates, calcium salixarates, calcium salicylates, calcium carboxylic acids, calcium phosphorus acids, calcium mono- and/or di-thiophosphoric acids, calcium alkyl phenols, calcium sulfur coupled alkyl phenol compounds, calcium methylene bridged phenols, magnesium phenates, magnesium sulfur containing phenates, magnesium sulfonates, magnesium calixarates, magnesium salixarates, magnesium salicylates, magnesium carboxylic acids, magnesium phosphorus acids, magnesium mono- and/or di-thiophosphoric acids, magnesium alkyl phenols, magnesium sulfur coupled alkyl phenol compounds, magnesium methylene bridged phenols, sodium phenates, sodium sulfur containing phenates, sodium sulfonates, sodium calixarates, sodium salixarates, sodium salicylates, sodium carboxylic acids, sodium phosphorus acids, sodium mono- and/or di-thiophosphoric acids, sodium alkyl phenols, sodium sulfur coupled alkyl phenol compounds, or sodium methylene bridged phenols.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, or phenols.

An overbased detergent of the lubricating oil composition may have a total base number (TBN) of about 200 mg KOH/gram or greater, or as further examples, about 250 mg KOH/gram or greater, or about 350 mg KOH/gram or greater, or about 375 mg KOH/gram or greater, or about 400 mg KOH/gram or greater. The TBN being measured by the method of ASTM D-2896.

Examples of suitable overbased detergents include, but are not limited to, overbased calcium phenates, overbased calcium sulfur containing phenates, overbased calcium sulfonates, overbased calcium calixarates, overbased calcium salixarates, overbased calcium salicylates, overbased calcium carboxylic acids, overbased calcium phosphorus acids, overbased calcium mono- and/or di-thiophosphoric acids, overbased calcium alkyl phenols, overbased calcium sulfur coupled alkyl phenol compounds, overbased calcium methylene bridged phenols, overbased magnesium phenates, overbased magnesium sulfur containing phenates, overbased magnesium sulfonates, overbased magnesium calixarates, overbased magnesium salixarates, overbased magnesium salicylates, overbased magnesium carboxylic acids, overbased magnesium phosphorus acids, overbased magnesium mono- and/or di-thiophosphoric acids, overbased magnesium alkyl phenols, overbased magnesium sulfur coupled alkyl phenol compounds, or overbased magnesium methylene bridged phenols.

The overbased calcium phenate detergents have a total base number of at least about 150 mg KOH/g, at least about 225 mg KOH/g, at least about 225 mg KOH/g to about 400 mg KOH/g, at least about 225 mg KOH/g to about 350 mg KOH/g or about 230 mg KOH/g to about 350 mg KOH/g, all as measured by the method of ASTM D-2896. When such detergent compositions are formed in an inert diluent, e.g. a process oil, usually a mineral oil, the total base number reflects the basicity of the overall composition including diluent, and any other materials (e.g., promoter, etc.) that may be contained in the detergent composition.

The overbased detergent may have a metal to substrate ratio of from 1.1:1, or from 2:1, or from 4:1, or from 5:1, or from 7:1, or from 10:1. In some embodiments, a detergent is effective at reducing or preventing rust in an engine or other automotive part such as a transmission or gear. The detergent may be present in a lubricating composition at about 0 wt % to about 10 wt %, or about 0.1 wt % to about 8 wt %, or about 1 wt % to about 4 wt %, or greater than about 4 wt % to about 8 wt %.

Extreme Pressure Agents: The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated wax; organic sulfides and polysulfides such as dibenzyldisulfide, bis(chlorobenzyl) disulfide, dibutyl tetrasulfide, sulfurized methyl ester of oleic acid, sulfurized alkyl phenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Friction Modifiers: The lubricating oil compositions herein also may optionally contain one or more friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanadine, alkanolamides, phosphonates, metal-containing compounds, glycerol esters, sulfurized fatty compounds and olefins, sunflower oil other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In some embodiments the friction modifier may be a long chain fatty acid ester. In another embodiment the long chain fatty acid ester may be a mono-ester, or a di-ester, or a (tri)glyceride. The friction modifier may be a long chain fatty amide, a long chain fatty ester, a long chain fatty epoxide derivatives, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g. carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685, herein incorporated by reference in its entirety.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291, herein incorporated by reference in its entirety.

A friction modifier may optionally be present in ranges such as about 0 wt % to about 10 wt %, or about 0.01 wt % to about 8 wt %, or about 0.1 wt % to about 4 wt %.

Molybdenum-containing component: The lubricating oil compositions herein also may optionally contain one or more molybdenum-containing compounds. An oil-soluble molybdenum compound may have the functional performance of an antiwear agent, an antioxidant, a friction modifier, or mixtures thereof. An oil-soluble molybdenum compound may include molybdenum dithiocarbamates, molybdenum dialkyldithiophosphates, molybdenum dithiophosphinates, amine salts of molybdenum compounds, molybdenum xanthates, molybdenum thioxanthates, molybdenum sulfides, molybdenum carboxylates, molybdenum alkoxides, a trinuclear organo-molybdenum compound, and/or mixtures thereof. The molybdenum sulfides include molybdenum disulfide. The molybdenum disulfide may be in the form of a stable dispersion. In one embodiment the oil-soluble molybdenum compound may be selected from the group consisting of molybdenum dithiocarbamates, molybdenum dialkyldithiophosphates, amine salts of molybdenum compounds, and mixtures thereof. In one embodiment the oil-soluble molybdenum compound may be a molybdenum dithiocarbamate.

Suitable examples of molybdenum compounds which may be used include commercial materials sold under the trade names such as Molyvan 822™, Molyvan™ A, Molyvan 2000™ and Molyvan 855™ from R. T. Vanderbilt Co., Ltd., and Sakura-Lube™ S-165, S-200, S-300, S-310G, S-525, S-600, S-700, and S-710 available from Adeka Corporation, and mixtures thereof. Suitable molybdenum components are described in U.S. Pat. No. 5,650,381; US RE 37,363 E1; US RE 38,929 E1; and US RE 40,595 E1, incorporated herein by reference in their entireties.

Additionally, the molybdenum compound may be an acidic molybdenum compound. Included are molybdic acid, ammonium molybdate, sodium molybdate, potassium molybdate, and other alkaline metal molybdates and other molybdenum salts, e.g., hydrogen sodium molybdate, MoOCl4, MoO2Br2, Mo2O3Cl6, molybdenum trioxide or similar acidic molybdenum compounds. Alternatively, the compositions can be provided with molybdenum by molybdenum/sulfur complexes of basic nitrogen compounds as described, for example, in U.S. Pat. Nos. 4,263,152; 4,285,822; 4,283,295; 4,272,387; 4,265,773; 4,261,843; 4,259,195 and 4,259,194; and WO 94/06897, incorporated herein by reference in their entireties.

Another class of suitable organo-molybdenum compounds are trinuclear molybdenum compounds, such as those of the formula Mo3SkLnQz and mixtures thereof, wherein S represents sulfur, L represents independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms may be present among all the ligands' organo groups, such as at least 25, at least 30, or at least 35 carbon atoms. Additional suitable molybdenum compounds are described in U.S. Pat. No. 6,723,685, herein incorporated by reference in its entirety.

The oil-soluble molybdenum compound may be present in an amount sufficient to provide about 0.5 ppm to about 2000 ppm, about 1 ppm to about 700 ppm, about 1 ppm to about 550 ppm, about 5 ppm to about 300 ppm, or about 20 ppm to about 250 ppm of molybdenum.

Transition Metal-containing compounds: In another embodiment, the oil-soluble compound may be a transition metal containing compound or a metalloid. The transition metals may include, but are not limited to, titanium, vanadium, copper, zinc, zirconium, molybdenum, tantalum, tungsten, and the like. Suitable metalloids include, but are not limited to, boron, silicon, antimony, tellurium, and the like.

In an embodiment, an oil-soluble transition metal-containing compound may function as antiwear agents, friction modifiers, antioxidants, deposit control additives, or more than one of these functions. In an embodiment the oil-soluble transition metal-containing compound may be an oil-soluble titanium compound, such as a titanium (IV) alkoxide. Among the titanium containing compounds that may be used in, or which may be used for preparation of the oils-soluble materials of, the disclosed technology are various Ti (IV) compounds such as titanium (IV) oxide; titanium (IV) sulfide; titanium (IV) nitrate; titanium (IV) alkoxides such as titanium methoxide, titanium ethoxide, titanium propoxide, titanium isopropoxide, titanium butoxide, titanium 2-ethylhexoxide; and other titanium compounds or complexes including but not limited to titanium phenates; titanium carboxylates such as titanium (IV) 2-ethyl-1-3-hexanedioate or titanium citrate or titanium oleate; and titanium (IV) (triethanolaminato) isopropoxide. Other forms of titanium encompassed within the disclosed technology include titanium phosphates such as titanium dithiophosphates (e.g., dialkyldithiophosphates) and titanium sulfonates (e.g., alkylbenzenesulfonates), or, generally, the reaction product of titanium compounds with various acid materials to form salts, such as oil-soluble salts. Titanium compounds can thus be derived from, among others, organic acids, alcohols, and glycols. Ti compounds may also exist in dimeric or oligomeric form, containing Ti—O—Ti structures. Such titanium materials are commercially available or can be readily prepared by appropriate synthesis techniques which will be apparent to the person skilled in the art. They may exist at room temperature as a solid or a liquid, depending on the particular compound. They may also be provided in a solution form in an appropriate inert solvent.

In one embodiment, the titanium can be supplied as a Ti-modified dispersant, such as a succinimide dispersant. Such materials may be prepared by forming a titanium mixed anhydride between a titanium alkoxide and a hydrocarbyl-substituted succinic anhydride, such as an alkenyl-(or alkyl) succinic anhydride. The resulting titanate-succinate intermediate may be used directly or it may be reacted with any of a number of materials, such as (a) a polyamine-based succinimide/amide dispersant having free, condensable —NH functionality; (b) the components of a polyamine-based succinimide/amide dispersant, i.e., an alkenyl-(or alkyl-) succinic anhydride and a polyamine, (c) a hydroxy-containing polyester dispersant prepared by the reaction of a substituted succinic anhydride with a polyol, aminoalcohol, polyamine, or mixtures thereof. Alternatively, the titanate-succinate intermediate may be reacted with other agents such as alcohols, aminoalcohols, ether alcohols, polyether alcohols or polyols, or fatty acids, and the product thereof either used directly to impart Ti to a lubricant, or else further reacted with the succinic dispersants as described above. As an example, 1 part (by mole) of tetraisopropyl titanate may be reacted with about 2 parts (by mole) of a polyisobutene-substituted succinic anhydride at 140-150° C. for 5 to 6 hours to provide a titanium modified dispersant or intermediate. The resulting material (30 g) may be further reacted with a succinimide dispersant from polyisobutene-substituted succinic anhydride and a polyethylenepolyamine mixture (127 grams+diluent oil) at 150° C. for 1.5 hours, to produce a titanium-modified succinimide dispersant.

Another titanium containing compound may be a reaction product of titanium alkoxide and $C_6$ to $C_{25}$ carboxylic acid. The reaction product may be represented by the following formula:

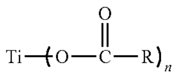

wherein n is an integer selected from 2, 3 and 4, and R is a hydrocarbyl group containing from about 5 to about 24 carbon atoms, or by the formula:

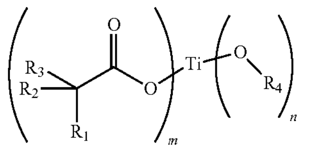

wherein m+n=4 and n ranges from 1 to 3, $R_4$ is an alkyl moiety with carbon atoms ranging from 1-8, $R_1$ is selected from a hydrocarbyl group containing from about 6 to 25 carbon atoms, and $R_2$ and $R_3$ are the same or different and are selected from a hydrocarbyl group containing from about 1 to 6 carbon atoms, or the titanium compound may be represented by the formula:

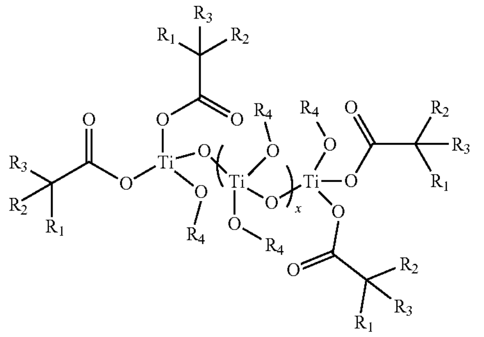

wherein x ranges from 0 to 3, $R_1$ is selected from a hydrocarbyl group containing from about 6 to 25 carbon atoms, $R_2$, and $R_3$ are the same or different and are selected from a hydrocarbyl group containing from about 1 to 6 carbon atoms, and $R_4$ is selected from a group consisting of either H, or $C_6$ to $C_{25}$ carboxylic acid moiety.

Suitable carboxylic acids may include, but are not limited to caproic acid, caprylic acid, lauric acid, myristic acid, palmitic acid, stearic acid, arachidic acid, oleic acid, erucic acid, linoleic acid, linolenic acid, cyclohexanecarboxylic acid, phenylacetic acid, benzoic acid, neodecanoic acid, and the like.

In an embodiment the oil soluble titanium compound may be present in the lubricating oil composition in an amount to provide from 0 to 3000 ppm titanium by weight or 25 to about 1500 ppm titanium by weight or about 35 ppm to 500 ppm titanium by weight or about 50 ppm to about 300 ppm.

Viscosity Index Improvers: The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 20120101017A1.

The lubricating oil compositions herein also may optionally contain one or more dispersant viscosity index improvers in addition to a viscosity index improver or in lieu of a viscosity index improver. Suitable viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt % to about 20 wt %, about 0.1 wt % to about 15 wt %, about 0.1 wt % to about 12 wt %, or about 0.5 wt % to about 10 wt %, of the lubricating oil composition.

Other Optional Additives: Other additives may be selected to perform one or more functions required of a lubricating fluid. Further, one or more of the mentioned additives may be multi-functional and provide functions in addition to or other than the function prescribed herein.

A lubricating oil composition according to the present disclosure may optionally comprise other performance additives. The other performance additives may be in addition to specified additives of the present disclosure and/or may comprise one or more of metal deactivators, viscosity index improvers, detergents, ashless TBN boosters, friction modifiers, antiwear agents, corrosion inhibitors, rust inhibitors, dispersants, dispersant viscosity index improvers, extreme pressure agents, antioxidants, foam inhibitors, demulsifiers, emulsifiers, pour point depressants, seal swelling agents and mixtures thereof. Typically, fully-formulated lubricating oil will contain one or more of these performance additives.

Suitable metal deactivators may include derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles; foam inhibitors including copolymers of ethyl acrylate and 2-ethylhexylacrylate and optionally vinyl acetate; demulsifiers including trialkyl phosphates, polyethylene glycols, polyethylene oxides, polypropylene oxides and (ethylene oxide-propylene oxide) polymers; pour point depressants including esters of maleic anhydride-styrene, polymethacrylates, polyacrylates or polyacrylamides.

Suitable foam inhibitors include silicon-based compounds, such as siloxane.

Suitable pour point depressants may include a polymethylmethacrylates or mixtures thereof. Pour point depressants may be present in an amount sufficient to provide from about 0 wt % to about 1 wt %, about 0.01 wt % to about 0.5 wt %, or about 0.02 wt % to about 0.04 wt % based upon the final weight of the lubricating oil composition.

Suitable rust inhibitors may be a single compound or a mixture of compounds having the property of inhibiting corrosion of ferrous metal surfaces. Non-limiting examples of rust inhibitors useful herein include oil-soluble high molecular weight organic acids, such as 2-ethylhexanoic acid, lauric acid, myristic acid, palmitic acid, oleic acid, linoleic acid, linolenic acid, behenic acid, and cerotic acid, as well as oil-soluble polycarboxylic acids including dimer and trimer acids, such as those produced from tall oil fatty acids, oleic acid, and linoleic acid. Other suitable corrosion inhibitors include long-chain alpha, omega-dicarboxylic acids in the molecular weight range of about 600 to about 3000 and alkenylsuccinic acids in which the alkenyl group contains about 10 or more carbon atoms such as, tetrapropenylsuccinic acid, tetradecenylsuccinic acid, and hexadecenylsuccinic acid. Another useful type of acidic corrosion inhibitors are the half esters of alkenyl succinic acids having about 8 to about 24 carbon atoms in the alkenyl group with alcohols such as the polyglycols. The corresponding half amides of such alkenyl succinic acids are also useful. A useful rust inhibitor is a high molecular weight organic acid.

The rust inhibitor, if present, can be used in an amount sufficient to provide about 0 wt % to about 5 wt %, about 0.01 wt % to about 3 wt %, about 0.1 wt % to about 2 wt %, based upon the final weight of the lubricating oil composition.

In general terms, a suitable lubricant including the neutral to overbased and sulfurized alkyl phenate product herein may include additive components in the ranges listed in the following table.

TABLE 2

Suitable Lubricating Compositions

| Component | Wt. % (Suitable Embodiments) | Wt. % (Suitable Embodiments) |
|---|---|---|
| Neutral/Overbased and sulfurized alkyl phenate | 0.02-5.0 | 0.2-2.0 |
| Succinimide Dispersant(s) | 0-8.0 | 1-6.0 |
| Antioxidant(s) | 0.1-5.0 | 0.01-3.0 |
| Detergent(s) | 0.0-15.0 | 0.2-8.0 |
| Ashless TBN booster(s) | 0.0-1.0 | 0.01-0.5 |
| Corrosion inhibitor(s) | 0.0-5.0 | 0.0-2.0 |
| Metal dihydrocarbyldithiophosphate(s) | 0.0-6.0 | 0.1-4.0 |
| Ash-free phosphorus compound(s) | 0.0-6.0 | 0.0-4.0 |
| Antifoaming agent(s) | 0.0-5.0 | 0.001-0.15 |
| Antiwear agent(s) | 0.0-1.0 | 0.0-0.8 |
| Pour point depressant(s) | 0.0-5.0 | 0.01-1.5 |
| Viscosity index improver(s) | 0.0-25.0 | 0.1-15.0 |
| Dispersant viscosity index improver(s) | 0.0-10.0 | 0.0-5.0 |
| Friction modifier(s) | 0.00-5.0 | 0.01-2.0 |
| Base oil | Balance | Balance |
| Total | 100 | 100 |

The percentages of each component above represent the weight percent of each component, based upon the weight of the final lubricating oil composition. The remainder of the lubricating oil composition consists of one or more base oils. Additives used in formulating the compositions described herein may be blended into the base oil individually or in various sub-combinations. However, it may be suitable to blend all of the components concurrently using an additive concentrate (i.e., additives plus a diluent, such as a hydrocarbon solvent). Fully formulated lubricants conventionally contain an additive package, referred to herein as a dispersant/inhibitor package or DI package, that will supply the characteristics that are required in the formulation.

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

For Comparative Examples where the sulfurization ratio is less than 500:1, the concentration of unsulfurized alkyl phenate was determined, for instance and as described in U.S. Pat. No. 8,933,022 B2, by reverse phase High Performance Liquid Chromatography (HPLC), such as when levels of unsulfurized alkyl phenate are at least about 0.3 weight percent or greater. In an exemplary HPLC method, samples were prepared by weighing about 80 to 120 mg into a 10 ml volumetric flask, diluting to the level mark with methylene chloride, and mixing until the sample is fully dissolved. The HPLC system used in the HPLC method included a HPLC pump, a thermostatted HPLC column compartment, HPLC fluorescence detector, and PC-based chromatography data acquisition system. An exemplary system is an Agilent 1200 HPLC with ChemStation software or equivalent. The HPLC column was a Phenomenex Luna C8(2) 150×4.6 mm 5 μm 100 Å or equivalent For the Comparative Examples, the following system settings were used in performing the analyses: Pump flow=1.0 ml/min, Maximum pressure=200 bars, Fluorescence wavelength: 225 excitation 313 emission: Gain=9, Column Thermostat temperature=25 C, Injection Size=1 μL of diluted sample, Elution type: Gradient, reverse phase, Gradient: 0-7 min 85/15 methanol/water switching to 100% methanol linear gradient, and Run time: 17 minutes For the Comparative Samples, the resulting chromatograph typically contains several peaks. Peaks due to the unsulfurized alkyl phenate typically elute at early retention times; whereas peaks due to sulfurized alkyl phenates elute at longer retention times. For purposes of quantitation, the area of the single largest peak of the unsulfurized alkyl phenate was measured, and this area was used to determine the concentration of the total unsulfurized alkyl phenate. The area of the chosen peak is compared to a calibration curve to determine the weight percent of the unsulfurized alkyl phenate from which the amounts of sulfurized alkyl phenate can be determined.

For inventive samples where the sulfurization ratio was 500:1 or greater, the methods above are not generally sensitive enough to measure such low levels of unsulfurized alkyl phenate/alkyl phenol. Rather, the measurement was performed consistent to the above method but modified using a sample having a target phenate concentration of 5 mg/ml and as follows using liquid chromatography-mass spectrometry (LC-MS) using single quad or triple quad MS or equivalent via an Agilent MS 6420 QQQ equipped with and Agilent MSD XT equipped with Agilent 1260 LC Column, such as a Supelco Ascentis Express RP Amide 2.7u, 100 mm×2.1 mmID column or equivalent equipment. For inventive sample measurement, the following system settings were used in the analysis: column temperature 45 C, flow rate of 0.3 ml/min, injection volume of 3 μl, and run time of 22 minutes. The MS system setting and conditions are as follows: ion source: ESI negative, mode SIM, gas temp of 300 C, gas flow 13 l/min, nebulizer 35 psi, capillary 3000 (v), fragmentor of 135, and peak width of 0.07. The percentage of unsulfurized alkyl phenol/alkyl phenate was determined using a MassHunter Quant Program or equivalent to generate a calibration curve and then to calculate the percent of unsulfurized alkyl phenol/phenate in the sample.

Comparative Example 1

As set forth in U.S. Pat. No. 8,933,002 B2, Example 1 and Example 3 therein describes sulfurization, neutralization, and overbasing of a tetrapropenylphenol with methanol and xylene, but such methods could only achieve a sulfurization ratio of 262:1 (i.e. residual unsulfurized TPP of 0.38).

As described in Example 1 of the '002 patent, a two-step process is illustrated for sulfurization of tetrapropenylphenol. As described in the '002 patent, step 1 was sulfurization of tetrapropenylphenol as follows: into a 4 liter round flask was charged 1620 g of tetrapropenyl phenol (available from Chevron Oronite Company LLC) at room temperature. The tetrapropenyl phenol was heated to 110° C. in 30 minutes. At 60° C., 14 g of a 50 wt. % potassium hydroxide aqueous solution was added under agitation. Next, 192 g of sulphur flakes (i.e. elemental sulfur) was added at 110° C. and the pressure was reduced to 680 mmHg. The reaction temperature was then increased to 180° C. in 30 minutes and the pressure was slowly decreased to 260 mmHg to facilitate the $H_2S$ release. The $H_2S$ gas formed was trapped in concentrated potassium hydroxide solution located before the vacuum pump. The reaction conditions were held for 2 hours and 45 minutes. The pressure was the further reduced to 50 mmHg in for 15 minutes and held under those conditions for another 3 hours. The sulfurized alkylphenol reaction product was allowed to cool down. The '002 patent describes that the obtained sulfurized alkylphenol had the following analysis: sulfur of 6.85 percent, potassium of 2646 ppm, a viscosity at 100° C. of 65.4 mm2/s, and TPP (that is, unreacted tetrapropenyl phenol and its calcium salt) of 26.5 percent.

Next, Example 1 of the '002 patent further described Step 2 that was the distillation of sulfurized alkylphenol from Step 1 as follows: the sulfurized alkylphenol reaction product obtained in step 1 was preheated to about 140° C. before being fed to a continuous 0.0385 $m^2$ wiped film evaporator at roughly 400 g/hour. The temperature of the evaporator was maintained at around 210° C. and the pressure around 1.5 mbar. The '002 patent then describes that the average distilled product had the following analytical properties: sulfur of about 10.3%, potassium of about 4293 ppm, a viscosity at 100° C. of about 402.8 mm2/s, and TPP of 0.31%

Then in Example 3 of the '002 patent, neutralizing, overbasing, and post processing of the product from the '002 patent Example 1 was described using methanol and xylene as follows: 243.2 g hydrated lime was added into a 5 liter double jacket glass reactor with 243.2 g of methanol and 876 g of xylene. Next, 713.4 g of a sulfurized tetrapropenylphenol from step 2 of Example 1 of the '002 patent was heated to about 80° C. and then diluted with 562 g of xylene. The mixture was added to the reactor in 30 minutes while the reaction temperature was increased from room temperature to 30° C. Then, the reaction mixture was cooled down to 25° C. in 20 minutes. Into the mixture was added 29.6 g of a 90/10 mole mixture of acetic acid and formic acid in 2 minutes. The reaction mixture temperature increased due to the exothermic reaction from 25° C. to 34° C. Then 24.4 g of $CO_2$ was added in 30 minutes while heating from 34° C. to 36° C. Next, 41.6 g of $CO_2$ was introduced in 66 minutes while heating from 36 to 42° C. A slurry composed of 60.8 g of hydrated lime, 60.8 g of methanol, 334 g of xylene was added in 1 minute to the reactor. Next, 51.4 g of additional $CO_2$ was added in 64 minutes while heating from 41° C. to 46° C. The temperature of the reaction mixture was raised to 65° C. in 26 minutes to start the methanol distillation. The temperature was further raised to 93° C. in 60 minutes. The temperature was further raised to 130° C. in 30 minutes. 550 g of 130 Neutral lube oil was added to the reaction mixture. The crude sediments were measured at 2.4 vol %. The crude product was centrifuged prior to performing a xylene distillation at 170° C. under 25 mBar during one hour.

Example 3 of the '002 patent then describes that the resulting product was degassed over 4 hours at 150° C., and that the resulting product included 9.56 percent calcium, 4.71 percent sulfur, potassium of 1876 ppm, a kinematic viscosity at 100° C. of 410.2 cSt, a TBN of 273 mg KOH/g and a residual content of unsulfurized tetrapropenylphenol (TPP) was reported as 0.38%, which is only a sulfurization ratio of 262:1.

Comparative Example 2

Similar to Comparative Example 1, U.S. Pat. No. 8,933,002 B2 Example 4 therein describes neutralization and overbasing of a tetrapropenylphenol with methanol, but such methods could only achieve a sulfurization ratio of 178:1. In this Example, 609.01 g of a sulfurized tetrapropenylphenol (Example 1 of U.S. Pat. No. 8,933,002) was charged into a 2 liter round flask. Next, 425.2 g of methanol and 0.2 g of foam inhibitor SI 200 available from Dow Corning were added to the reactor. The reaction mixture was warmed up to 60° C. under agitation. During this step, 78.5 g of hydrated lime was introduced along with 300 g of 100N diluent oil. At 60° C., 4.6 g of a 50/50 by weight mixture of acetic acid and formic acid was added. The neutralization was held during 210 minutes at 60° C. and at atmospheric pressure. The methanol was evaporated by reducing slowly the pressure to 30 mm Hg in about 2 hours. During this step, 354 g of lube oil was added dropwise. The distillation was held one hour at 60° C. under 30 mm Hg. The crude sediment of the neutralized calcium salt of the sulfurized alkylhydroxyaromatic was measured at 0.4 vol %. The product was filtered on a büchner to eliminate the unreacted lime.

U.S. Pat. No. 8,933,002 further describes that the obtained product was degassed over 4 hours at 150° C. under air and that the product had the following analysis: 3.17% calcium, 4.86% sulfur, K: 1827 ppm, a kinematic viscosity at 100° C. of 80.8 cSt, a TBN of 89 mg KOH/g and an unsulfurized tetrapropenylphenol (TPP) content was reported as 0.56%, which was a sulfurization ratio of only 178:1.

Comparative Example 3

A tetrapropylene calcium phenate composition having a TBN of 118, about 4.26 weight percent calcium, and 1.8 weight percent of unsulfurized tetrapropylene phenol/phenate obtained from a catalyzed sulfur monochloride was overbased at 165° C. for 3 hours and then vacuum distilled for 1 hour at 200° C. After overbasing and distillation, the product had a TBN of 314, but now had 4.4 weight percent of the unsulfurized tetrapropylene phenate/phenol.

Comparative Example 4

As set forth in U.S. Pat. No. 4,973,411, Example 1 therein describes a sulfurized phenate product, but such method, when tested using the measurement methods of the present application, only achieves residual unsulfurized alkyl phenol of about 0.3 to about 0.5 weight percent and, thus, only achieve a sulfurization ratio of about 300:1. Example 1 of the '411 patent utilized sulfur dichloride from Sigma Aldrich with 80 weight percent of sulfur dichloride and 20 percent of impurities including sulfur monochloride Example 1 of U.S. Pat. No. 4,973,411 was duplicated as follows: a charge of about 192 parts of dodecylphenol by weight was added into a 3-liter four neck reaction flask along with about 840 parts of isooctane or heptane. Then, nitrogen gas was bubbled through the mixture at a rate of about 400 ml/min. Next, about 51 parts of the above described sulfur dichloride (80% $SCl_2$ and 20% $S_2Cl_2$) was added via an addition funnel to keep the reaction temperature close to room temperature. The reactants were stirred for about 5 minutes and then the reaction was heated to about 80° C. for half an hour. Then, the reactants were cooled to about 45° C. Next, about 216 parts of 100 P pale oil, plus about 115 parts of methanol, and about 105 parts of Ca (OH) 2 were added; the nitrogen gas was stopped, and the mixture was stirred for one hour at about 55° C. to about 57° C. The temperature was maintained and $CO_2$ was bubbled at an appropriate rate between about 200 to about 300 ml/min for approximately about 77 minutes. Finally, the crude product was filtered and the solvent stripped at approximately 100° C. under vacuum. The duplicated product had about 8.8 weight percent calcium, about 3.4 weight percent sulfur, and a KV100 of about 143, and a TBN of 232 that was consistent with the final product as reported in the '411 patent.

While U.S. Pat. No. 4,973,411 does not disclose or suggest any impact of a mol ratio between the sulfur source and the dodecylphenol, the mol ratio of the sulfur source provided from the 80 weight percent sulfur dichloride and 20 weight percent sulfur monochloride to the dodecylphenol, in this Example, was calculated to be 0.64:1.

When evaluated for residual unsulfurized alkylphenol using the test methods of the present application including either reverse phase High Performance Liquid Chromatography (HPLC) and/or a liquid chromatography-mass spectrometry (LC-MS), as described above, the residual unsulfurized alkylphenol levels of Example 1 from U.S. Pat. No. 4,973,411 was measured at 0.39 weight percent.

Example 1

The results of inventive low temperature processes to produce an overbased and sulfurized tetrapropylene alkylated phenate product having high sulfurization ratios using the methods of the present application is set forth in the Tables below. For this Example, three different sulfurized tetrapropylene alkylated phenols were first prepared by reacting about 720 grams of tetrapropylene phenol with about 241 grams of sulfur monochloride as follows:

S1: the tetrapropylene phenol was charged to a kettle and the sulfur monochloride added dropwise at about 100° C., thereafter the temperature was increased to about 180° C. and held for about 1 hour, then increased to about 190° C. and held for about 1 hour, after which a vacuum strip was performed at about 200° C. for about 1 hour, the mixture was then cooled to about 150° C., and about 252 grams of process oil added. After sulfurization, the intermediate sulfurized product had a sulfurization ratio of about 499:1.

S2: the tetrapropylene phenol was charged to a kettle along with about 100 grams of heptane and the sulfur monochloride was added dropwise at about 40° C., thereafter the temperature was increased to about 100° C. and a full vacuum strip was performed to distill the heptane over about 1 hour, after which a vacuum strip was performed at about 200° C. for about 1 hour, then cooled to about 150° C. and about 252 grams of process oil added. After sulfurization, the intermediate sulfurized product had a sulfurization ratio of about 1110:1.

S3: the tetrapropylene phenol was charged to a kettle along with about 100 grams of heptane and the sulfur monochloride was added dropwise at about 40° C., thereafter the temperature was increased to a about 100° C. and a full vacuum strip was performed to distill the heptane over about 1 hour, and then about 252 grams of process oil added. After sulfurization, the intermediate sulfurized product had a sulfurization ratio of about 2499:1.

Each sulfurized tetrapropylene phenol S1, S2, or S3 was then neutralized with calcium oxide in the presence of an ammonium sulfonate composition, a solvent system, and process oil as set forth in Table 4. The neutralized composition was then overbased in the solvent system by treatment with gaseous carbon dioxide at about 208 sccm as set forth in Tables 5 and 6. Table 3 provides the characterization of the neutralized and overbased product.

TABLE 3

| Sample | Sulfurized Alkyl Phenol | TBN | Calcium % | Unsulfurized Alkyl Phenol* % | Sulfurization Ratio** | Sulfur % |
|---|---|---|---|---|---|---|
| A | S1 | 113 | 4.43 | 0.08 | 1249:1 | 4.64 |
| B | S1 | 174 | 6.26 | 0.08 | 1249:1 | — |
| C | S1 | 217 | 8.12 | 0.07 | 1427:1 | 4.98 |
| D | S1 | 151 | 5.61 | 0.08 | 1249:1 | 5.22 |
| E | S1 | 229 | 8.32 | 0.08 | 1249:1 | 4.97 |
| F | S2 | 196 | 7.44 | 0.05 | 1999:1 | 5.04 |
| G | S3 | 211 | 7.95 | 0.03 | 3332:1 | 4.73 |
| H | S3 | 126 | 4.67 | 0.03 | 3332:1 | 6.21 |
| I | S3 | 139 | 5.29 | 0.02 | 4999:1 | 4.0 |
| J | S3 | 98 | 3.90 | 0.03 | 3332:1 | 5.74 |
| K | S2 | 248 | 9.51 | 0.05 | 1999:1 | 4.72 |

*Unsulfurized alkyl phenol refers to both unsulfurized alkyl phenate and any unsulfurized alkyl phenol in the product.

**For example, the sulfurization ratio of Sample A was determined from 99.92% sulfurized alkyl phenate in the sample and 0.08% unsulfurized alkyl phenate/phenol in the sample, which resulted in a weight ratio of 99.92:0.08 or 1249:1

TABLE 4

| | Neutralization | | | | | | | |
|---|---|---|---|---|---|---|---|---|
| | Sulfurized Alkyl Phenol, grams | CaO, grams | Heptane, grams | Xylene, grams | Water, grams | MeOH, grams | Temp, C. | Time, hours |
| A | 92.2 | 56.0 | — | 345 | 26.45 | 16.68 | 83 | 2 |
| B | 92.2 | 56.1 | 350 | — | 26.45 | 16.68 | 83 | 2 |
| C | 92.2 | 56.1 | 355 | — | 26.45 | 16.68 | 83 | 2 |
| D | 92.9 | 74.6 | 367 | — | 30.1 | 18.8 | 83 | 2 |
| E | 93.6 | 83.2 | 375 | — | 26.66 | 17.58 | 83 | 2 |
| F | 184.8 | 113.4 | 715 | — | 52.9 | 33.36 | 73 | 3 |
| G | 184.4 | 112.7 | 500 | — | 51.8 | 31.4 | 73 | 3 |
| H | 219.7 | 112.4 | 400 | — | 53.24 | 35.35 | 73 | 3 |
| I | 205.4 | 112.8 | 430.5 | — | 52.98 | 34.52 | 73 | 3 |
| J | 185.0 | 111.9 | 506.9 | — | 53.02 | 33.65 | 73 | 3 |
| K | 184.6 | 112.8 | 503 | — | 51.9 | 31.5 | 73 | 3 |

TABLE 5

| Further processing before Overbasing | |
|---|---|
| A | — |
| B | — |
| C | Dean Stark trap adding 17 g water up to 104 C; vacuum strip for 10 min |
| D | Vacuum strip at 83 C for 30 min |
| E | Dean Stark trap adding 17 g water to 104 C |
| F | Dean Stark trap adding 31 g water to 82.2 C |
| G | Dean Stark trap adding 14.7 g water to 83.3 C |
| H | Dean Stark trap adding 0 g water to 92 C |
| I | Dean Stark trap adding 15.2 g water to 85.4 C |
| J | Dean Stark trap adding 0 g water to 86 C |
| K | Dean Stark trap adding 0 g water to 92 C |

TABLE 6

| | Overbasing | | |
|---|---|---|---|
| | Pre-additions | Temp, C. | Time, min |
| A | 120 mL Xylene | 70 | 105 |
| B | 100 mL heptane | 80 | 80 |
| C | 12 g water, 120 g heptane | 42 | 80 |
| D | 12 g water, 300 g heptane | 42 | 80 |
| E | 12 g water, 120 mL heptane, 20.5 g CaO | 42 | 150 |
| F | 195 g heptane, 17.78 g CaO, 20 g water | 42 | 145 |
| G | 195 g heptane, 27 g CaO, 70 g water | 42* | 168 |
| H | 9 g neutral CaS, 29 g CaO, 100 g heptane, 70 g water | 42 | 217 |
| I | 132.4 g process oil, 20.7 g CaO, 68.5 g water, 8.5 g neutral CaS | 42 | 195 |
| J | 195 g heptane, 27 g CaO, 70 g water | 42 | 180 |
| K | 29.1 g Ca(OH)2 | 42 | 157 |

*21 g CaO added throughout overbasing

After overbasing, the samples were subjected to filtering and vacuum stripping at temperatures not exceeding about 140° C. to produce the sulfurized alkyl phenate products as summarized above in Table 3.

Example 2

Further experiments were performed to duplicate Example 1 of U.S. Pat. No. 8,933,002 B2 for the sulfurization of tetrapropenylphenol. Sulfurization in Step 1 of Example 1 of the '002 patent was followed and the resulting intermediate product had 6.88 percent sulfur, a KV100 of 56.8 mm2/s, potassium of 1958 ppm, and an unsulfurized tetrapropenylphenol content of 30.4 percent.

Distillation using a wiped film evaporator consistent with Step 2 of Example 1 of the '002 patent was then conducted on the intermediate product to produce a sulfurized tetrapropylene alkylated phenate product having high sulfurization ratios (i.e. low levels of unreacted or unsulfurized tetrapropylene phenol) except the vacuum was 1100 mTorr and the feed rate was 360 g/hour. The resulted product had 10.18 percent sulfur, a KV100 of 360 mm2/s, 3133 ppm of potassium, and 0.05% of unreacted or unsulfurized tetrapropylene phenol or a high sulfurization ratio of 1999:1.

Example 3

The duplicated sulfurized alkylphenol from Example 2 above was then neutralized and overbased consistent with Example 3 of U.S. Pat. No. 8,933,002 B2 except the solvent was heptane and methanol and the neturalization, overbasing, and post processing was conducted at low temperatures not to exceed about 100° C.

The solvent mixture for this Example was about 90% heptane and about 10% methanol. The crude product of Example 2 above was centrifuged at temperatures not to exceed 100° C. and then the product was degassed at temperatures not to exceed 100° C. to form the final sulfurized product having the following: 4.24% sulfur, a KV100 of 298.8 mm2/s, potassium of 1048 ppm, an unsulfurized alkylphenol content of less than 0.03% (that is, undetectable amounts or a sulfurization ratio of 3333:1 or higher), a TBN of 270.4, and a calcium content of 10.52 percent.

When comparing the results of this Example using heptane/methanol solvent system relative to Comparative Example 2 above (using the methods of U.S. Pat. No. 8,933,002 and the methanol/xylene solvent and high temperature post processing), the impact of solvent selection and low temperature processing and, in particular, low temperature post processing discovered herein can be shown. In Comparative Example 2 with the methanol/xylene solvent system and high temperature post processing of the '002 patent, the level of unreacted TPP increased after the neutralizing, overbasing, and post processing, but in this Example using the heptane/methanol solvent and low temperature post processing, the level of unreacted TPP decreased even further in the final product.

This temperature dependency on formation of unreacted TPP (that is, the regeneration of unsulfurized TPP during processing) is also shown in the graph of FIG. 1 that exemplifies the reaction kinetics of the regeneration of unsulfurized TPP based on temperature. As shown in FIG. 1, when the temperatures are maintained at about 100° C. and below (such as about 80° C.) during processing, the level of unreacted or unsulfurized TPP is not regenerated.

Example 4

Further experiments were performed to produce a sulfurized tetrapropylene alkylated phenate product having high sulfurization ratios (i.e. low levels of unreacted or unsulfurized tetrapropylene phenol) using the methods of the present application and as set forth in Table 7 below. In this Example, the sulfur source used was a mixture of about 67 weight percent of sulfur dichloride ($SCl_2$) and about 33 weight percent of sulfur monochloride ($S_2Cl_2$) at different mol ratios of the sulfur source to the tetrapropylene phenol (TPP) and generally using the sulfurization methods of Comparative Example 1 and wherein any post processing occurred at temperatures of about 100° C. or below.

Residual levels of unreacted tetrapropylene phenol were measured using LCMS as discussed above to detect unreacted or unsulfurized alkyl phenol in the product and the results are provided in Table 7 below. The LCMS technique has a detection limit of 0.03 weight percent. As shown in Table 7, ratios of the sulfur source to the alkyl phenol of at least 0.7 or higher result in undetectable levels of unreacted or unsulfurized tetrapropylene phenol in the sulfurized product and/or when combined with the low temperature processing of the disclosure herein.

TABLE 7

| Mole Ratio Sulfur Chloride to TPP | Residual TPP, wt % |
|---|---|
| 0.4 | 8.9 |
| 0.5 | 3.8 |
| 0.55 | 1.7 |
| 0.6 | 0.37 |

TABLE 7-continued

| Mole Ratio Sulfur Chloride to TPP | Residual TPP, wt % |
|---|---|
| 0.65 | 0.08 |
| 0.66 | Predicted to be about 0.05 |
| 0.7 | <0.03 |
| 0.75 | <0.03 |
| 0.8 | <0.03 |

Any neutralizing and/or overbasing consistent with the present disclosure may be conducted on the compositions of this Example.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A process for preparing a sulfurized alkyl phenate product to achieve a high sulfurization ratio of sulfurized alkyl phenate to unsulfurized alkyl phenate, the process comprising:

sulfurizing an alkyl phenol with a source of sulfur to provide a sulfurized alkyl phenol, wherein the alkyl phenol is derived from an alkylation of a phenol and wherein a mol ratio of the sulfur source to the alkyl phenol is about 0.66 to about 3.5;

neutralizing and optionally overbasing the sulfurized alkyl phenol in the presence of a solvent to provide a sulfurized alkyl phenate composition, wherein the neutralizing and the optional overbasing is at a temperature not exceeding about 140° C. to achieve a sulfurization ratio of about 500:1 or greater; and post processing the sulfurized alkyl phenate composition to obtain the sulfurized alkyl phenate product, wherein the post processing is at temperatures not to exceed about 140° C. to maintain the sulfurization ratio of about 500:1 or greater.

2. The process for preparing the sulfurized alkyl phenate of claim 1, wherein the source of sulfur includes elemental sulfur, sulfur monochloride, sulfur dichloride, hydrogen sulfide, sulfur dioxide, sulfide hydrates, or combinations thereof.

3. The process for preparing the sulfurized alkyl phenate of claim 1, wherein a mol ratio of the sulfur source to the alkyl phenol is about 0.7 to about 2.

4. The process for preparing the sulfurized alkyl phenate of claim 1, wherein the sulfur source is sulfur monochloride and sulfur dichloride.

5. The process for preparing the sulfurized alkyl phenate of claim 1, wherein the solvent is one more solvents having a boiling point of about 100° C. or less at about 1000 to about 40 mbars.

6. The process for preparing the sulfurized alkyl phenate of claim 5, wherein the solvent is about 85 to about 95 weight percent heptane and about 5 to about 15 weight percent methanol.

7. The process for preparing the sulfurized alkyl phenate of claim 1, wherein the neutralizing and/or the optional overbasing includes contacting the sulfurized alkyl phenol with an alkali or alkaline earth metal salt at a temperature not to exceed about 140° C. and wherein the alkali or alkaline earth metal salt is lithium hydroxide, potassium hydroxide, sodium hydroxide, magnesium hydroxide, calcium hydroxide, barium hydroxide, aluminum hydroxide, lithium oxide, magnesium oxide, calcium oxide, barium oxide, or combinations thereof.

8. The process for preparing the sulfurized alkyl phenate of claim 1, wherein the process does not remove residual unsulfurized alkyl phenate between the sulfurizing, the neutralizing, and/or the optional overbasing.

9. The process for preparing the sulfurized alkyl phenate of claim 1, wherein the sulfurized alkyl phenate product has a total base number of about 100 to about 400 mg KOH/g as measured by the method of ASTM D-2896.

10. The process for preparing the sulfurized alkyl phenate of claim 1, wherein the sulfurizing occurs in the absence of a base.

11. The process for preparing the sulfurized alkyl phenate of claim 1, wherein the sulfurized alkyl phenol is neutralized and overbased.

12. The process for preparing the sulfurized alkyl phenate of claim 1, wherein the sulfurized alkyl phenate product has less than about 0.2 weight percent of unsulfurized alkyl phenate and/or unsulfurized alkyl phenol.

13. A sulfurized alkyl phenate product prepared by the methods of claim 1.

14. A metal phenate detergent having a high sulfurization ratio of sulfurized alkyl phenate to unsulfurized alkyl phenate or unsulfurized alkyl phenol, the metal phenate detergent comprising:

a sulfurized alkyl phenate obtained from a source of sulfur and an alkyl phenol and having a total base number of about 50 to about 400 mg KOH/g as measured by the method of ASTM D-2896, wherein a mol ratio of a sulfur source to the alkyl phenol is about 0.66 to about 3.5; up to about 100,000 ppm of alkali or alkaline metal and up to about 65,000 ppm of sulfur; and a sulfurization ratio of about 500:1 to about 5500:1 with no more than about 900 ppm of unsulfurized alkyl phenate and/or unsulfurized alkyl phenol.

15. The metal phenate detergent of claim 14, wherein the alkyl phenate is derived from an alkylation of a phenol with one or more C6 to C36 alkylene groups.

16. The metal phenate detergent of claim 15, wherein the alkylene groups are oligomers.

17. The metal phenate detergent of claim 16, wherein the oligomers are derived from ethylene, propylene, butylene, isobutylene, pentene, or combinations thereof.

18. The metal phenate detergent of claim 14, wherein the sulfurized alkyl phenate detergent has a total base number of about 90 to about 250 mg KOH/g as measured by the method of ASTM D-2896.

19. The metal phenate detergent of claim 14, wherein the sulfurized alkyl phenate has less than about 50 percent of alkyl substitution at the ortho position.

20. A lubricating oil composition comprising the metal phenate detergent of claim 14 and one or more base oils of lubricating viscosity.

* * * * *